United States Patent
Gordeev et al.

(10) Patent No.: US 7,101,874 B2
(45) Date of Patent: Sep. 5, 2006

(54) ANTIMICROBIAL DIHYDROTHIAZINE AND DIHYDROTHIOPYRAN OXAZOLIDINONES

(75) Inventors: Mikhail F. Gordeev, Castro Valley, CA (US); Adam Renslo, Oakland, CA (US); Gary W. Luehr, Hayward, CA (US); Stuart Lam, San Francisco, CA (US); Neil E. Westlund, Cambridge, MA (US); Dinesh Vinoobhai Patel, Fremont, CA (US)

(73) Assignee: Pharmacia and Upjohn Company, Kalamazoo, MI (US)

( * ) Notice: Subject to any disclaimer, the term of this patent is extended or adjusted under 35 U.S.C. 154(b) by 0 days.

(21) Appl. No.: 11/062,990

(22) Filed: Feb. 22, 2005

(65) Prior Publication Data

US 2005/0143376 A1 Jun. 30, 2005

Related U.S. Application Data

(62) Division of application No. 10/347,640, filed on Jan. 21, 2003, now Pat. No. 6,884,813.

(60) Provisional application No. 60/351,495, filed on Jan. 24, 2002.

(51) Int. Cl.
*C07D 417/04* (2006.01)
*C07D 417/14* (2006.01)
*A61K 31/541* (2006.01)
*A61P 31/04* (2006.01)

(52) U.S. Cl. ............... 514/227.8; 544/56; 544/58.1; 544/58.6; 544/58.7

(58) Field of Classification Search ........ 544/56, 544/58.1, 58.6, 58.7; 514/227.8
See application file for complete search history.

(56) References Cited

U.S. PATENT DOCUMENTS

| 5,688,712 A | 11/1997 | Ema et al. |
| 5,968,962 A | 10/1999 | Thomas et al. |
| 5,981,528 A | 11/1999 | Gravestock |
| 2001/0041728 A1 | 11/2001 | Hester, Jr. et al. |

FOREIGN PATENT DOCUMENTS

| WO | WO95/07271 | 3/1995 |
| WO | WO02/81470 | 10/2002 |

OTHER PUBLICATIONS

Barbchyn, et al., Journal of Medicinal Chemistry. 1996, 39, 680-685.

*Primary Examiner*—Kahsay Habte
(74) *Attorney, Agent, or Firm*—Lucy X. Yang

(57) ABSTRACT

The present invention provides a compound of formula I

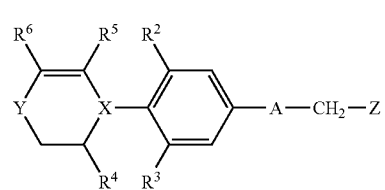

or a pharmaceutically acceptable salt thereof wherein Y is $-S(=O)_n-$, $-S(=NR^8)-$, or $-S(=NR^8)(=O)-$; Z is $-NHC(=O)R^1$, $-NHC(=S)R^1$, $-NH\text{-het}^1$, $-O\text{-het}^1$, $-S\text{-het}^1$, or $-\text{het}^2$. The compounds of formula I are useful as antibacterial agents.

24 Claims, No Drawings

ANTIMICROBIAL DIHYDROTHIAZINE AND DIHYDROTHIOPYRAN OXAZOLIDINONES

CROSS-REFERENCE TO RELATED APPLICATION

This application is a divisional application of U.S. patent application Ser. No. 10/347,640 filed on 21 Jan. 2003, which claims the benefit of provisional application U.S. Ser. No. 60/351,495 filed 24 Jan. 2002, all of which are incorporated herein by reference.

FIELD OF THE INVENTION

The present invention relates to novel dihydrothiazine and dihydrothiopyran oxazolidinones and their preparations. These compounds have potent activities against Gram-positive and Gram-negative bacteria.

BACKGROUND OF THE INVENTION

The oxazolidinone antibacterial agents are a novel synthetic class of antimicrobials with potent activity against a number of human and veterinary pathogens, including Gram-positive aerobic bacteria such as multiply-resistant staphylococci and streptococci, anaerobic organisms such as bacteroides and clostridia species, and acid-fast organisms such as *Mycobacterium tuberculosis* and *Mycobacterium avium*.

However, oxazolidinones generally do not demonstrate an activity at a useful level against aerobic Gram-negative organisms. Thus, the use of these oxazolidinone antibacterial agents is limited to infectious states due to Gram-positive bacteria. Accordingly, it is among the objects of the present invention to provide pharmaceutical compounds which have broader antibacterial activity including the activity against aerobic Gram-negative organisms. We have now discovered that the oxazolidinones of the present invention increase the spectrum of activity to include gram-negative organisms such as *Haemophilus influenza* and *Moraxella catarrhalis*.

INFORMATION DISCLOSURE

U.S. Pat. No. 5,968,962 discloses phenyloxazolidinones having a C—C bond to 4–8 membered heterocyclic rings.

U.S. Pat. No. 5,688,712 discloses substituted oxazine and thiazine oxazolidinone antimicrobials.

U.S. Pat. No. 5,981,528 discloses antibiotic oxazolidinone derivatives.

SUMMARY OF THE INVENTION

The present invention provides a compound of formula I

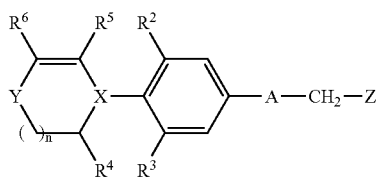

or a pharmaceutically acceptable salt thereof wherein:
A is a structure i, ii, iii, or iv

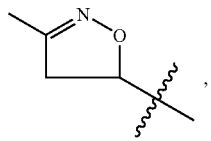

i

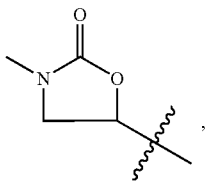

ii

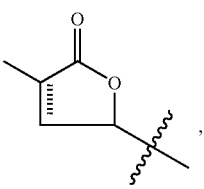

iii

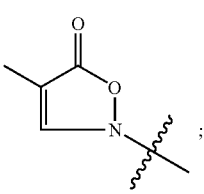

iv

X is N, or $CR^7$;
Y is
  (a) $S(=O)_n$,
  (b) $S(=NR^8)$, or
  (c) $S(=NR^8)(=O)$;
Z is
  (a) $NHC(=O)R^1$,
  (b) $NHC(=S)R^1$,
  (c) $NH\text{-}het^1$,
  (d) $O\text{-}het^1$,
  (e) $S\text{-}het^1$, or
  (f) $het^2$;
$R^1$ is
  (a) H,
  (b) $NH_2$,
  (c) $NHC_{1\text{-}4}alkyl$,
  (d) $C_{1\text{-}4}alkyl$,
  (e) $C_{2\text{-}4}alkenyl$,
  (f) $-(CH_2)_nC(=O)C_{1\text{-}4}alkyl$,
  (g) $OC_{1\text{-}4}alkyl$,
  (h) $SC_{1\text{-}4}alkyl$, or
  (i) $(CH_2)_nC_{3\text{-}6}cycloalkyl$;
$R^2$ and $R^3$ are independently
  (a) H,
  (b) Cl,
  (c) F,
  (d) $CH_3$,
  (e) $NH_2$, or
  (f) OH;
$R^4$ is
  (a) H,
  (b) F,
  (c) $C_{1\text{-}4}alkyl$, (d) OC$_{1-4}$alkyl,
(e) SC$_{1-4}$alkyl, or
(f) NHC$_{1-4}$alkyl;

R$^5$ is
(a) H,
(b) C$_{1-4}$alkyl,
(c) OC$_{1-4}$alkyl,
(d) SC$_{1-4}$alkyl, or
(e) NHC$_{1-4}$alkyl;

R$^6$ is
(a) H,
(b) F,
(c) Cl,
(d) NH$_2$,
(e) OH,
(f) CN,
(g) C$_{1-4}$alkyl,
(h) OC$_{1-4}$alkyl,
(i) C$_{1-4}$alkyl-W—C$_{1-4}$alkyl,
(j) NHC$_{1-4}$alkyl,
(k) (CH$_2$)$_n$C$_{3-6}$cycloalkyl,
(l) C(=O)C$_{1-4}$alkyl,
(m) OC(=O)C$_{1-4}$alkyl,
(n) C(=O)OC$_{1-4}$alkyl,
(O) S(O)$_n$C$_{1-4}$alkyl, or
(p) C(=O)NHC$_{1-4}$alkyl;

R$^7$ is
(a) H,
(b) CH$_3$,
(c) F, or
(d) OH;

R$^8$ is
(a) H,
(b) C$_{1-4}$alkyl,
(c) C(=O)C$_{1-4}$alkyl,
(d) C(=O)NHC$_{1-4}$alkyl,
(e) OC(=O)C$_{1-4}$alkyl,
(f) C(=O)OC$_{1-4}$alkyl,
(g) S(O)$_n$C$_{1-4}$alkyl, or
(h) C$_{1-4}$alkyl-W-C$_{1-4}$alkyl;

W is O or S;

aryl is phenyl, biphenyl, or naphthyl, optionally substituted with halo, —C$_{1-4}$alkyl, —OH, —OC$_{1-4}$alkyl, —S(O)$_n$C$_{1-4}$alkyl, and —C$_{1-4}$alkyl-NH$_2$;

het$^1$ is a C-linked five-(5) or six-(6) membered heterocyclic ring having 1–4 heteroatoms selected from the group consisting of oxygen, sulfur, and nitrogen;

het$^2$ is a N-linked five-(5) or six-6) membered heterocyclic ring having at least one nitrogen atom, and optionally having one oxygen or sulfur atom;

at each occurrence n is independently 0, 1, or 2;

at each occurrence, alkyl, alkenyl, or cycloalkyl is optionally substituted with one, two, or three halo, OH, OC$_{1-4}$alkyl, aryl, het$^1$, or het$^2$;

and with the proviso that where X is N, R$^4$ is other than F.

In another aspect, the present invention also provides:

a pharmaceutical composition comprising a compound of formula I or a pharmaceutically acceptable salt thereof, and a pharmaceutically acceptable carrier, a method for treating gram-positive microbial infections in a mammal in need of such treatment by administering to the subject in need a therapeutically effective amount of a compound of formula I or a pharmaceutically acceptable salt thereof, and a method for treating gram-negative microbial infections in a mammal in need of such treatment by administering to the subject in need a therapeutically effective amount of a compound of formula I or a pharmaceutically acceptable salt thereof.

The invention also provides some novel intermediates and processes that are useful for preparing compounds of formula I.

DETAILED DESCRIPTION OF THE INVENTION

The following definitions are used, unless otherwise described.

The term alkyl, alkenyl, etc. refer to both straight and branched groups, but reference to an individual radical such as "propyl" embraces only the straight chain radical, a branched chain isomer such as "isopropyl" being specifically referred to.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

The term "halo" refers to fluoro (F), chloro (Cl), bromo (Br), or iodo (I).

Aryl refers to phenyl, biphenyl, or naphthyl, optionally substituted with halo, —C$_{1-4}$alkyl, —OH, —OC$_{1-4}$alkyl, —S(O)$_n$C$_{1-4}$alkyl, and —C$_{1-4}$alkyl-NH$_2$.

aryl is phenyl, biphenyl, or naphthyl, optionally substituted with halo, —C$_{1-4}$alkyl, —OH, —OC$_{1-4}$alkyl, —S(O)$_n$C$_{1-4}$alkyl, and —C$_{1-4}$alkyl-NH$_2$;

The term "het$^1$" is a C-linked five-(5) or six-(6) membered heterocyclic ring having 1–4 heteroatoms selected from the group consisting of oxygen, sulfur, and nitrogen. Het$^1$ may be substituted where it is suitable; and may be an ortho-fused bicyclic heterocycle of about eight to ten ring atoms derived there from, particularly a benz-derivative or one derived by fusing a propylene, trimethylene, or tetramethylene diradical thereto.

The term "het$^2$" is a N-linked five-(5) or six-6) membered heterocyclic ring having at least one nitrogen atom, and optionally having one oxygen or sulfur atom.

Examples of "het$^1$" include, but are not limited to, pyridine, thiophene, furan, pyrazole, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,5-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, or 1,2,4-dithiazolone.

Examples of "het$^2$" include, but are not limited to, pyrrolyl, imidazolyl, pyrazolyl, triazolyl, tetrazolyl or isoaxzolinonyl.

Mammal refers to human or animals including livestock and companion animals.

"Optional" or "optionally" means that the subsequently described event or circumstance may, but need not, occur, and that the description includes instances where the event or circumstance occurs and instances in which it does not.

A "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

The compounds of the present invention are generally named according, to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents.

Specifically, alkyl denotes both straight and branched groups; but reference to an individual radical such as "propyl" embraces only the straight chain radical, a branched chain isomer such as "isopropyl" being specifically referred to. Specifically, $C_{1-4}$alkyl can be methyl, ethyl, propyl, isopropyl, butyl, iso-butyl, sec-butyl, and their isomeric forms thereof.

Specifically, $C_{2-4}$alkenyl can be vinyl, propenyl, allyl, butenyl, and their isomeric forms thereof; $C_{3-6}$ cycloalkyl can cyclopropyl, cyclobutyl, cyclopentyl, cyclohexyl, and their isomeric forms thereof.

Specifically, halo is fluoro (F), or chloro (Cl).

Specifically, $R^1$ is $C_{1-4}$alkyl, optionally substituted with one, two or three fluoro (F), or chloro (Cl).

Specifically, $R^1$ is $CH_3$, or $CH_2CH_3$.

Specifically $R^1$ is $CHF_2$, or $CHCl_2$.

Specifically, $R^1$ is $CH_2CF_3$, or $CF_2CH_3$,

Specifically, $R^1$ is —CH=CH-aryl.

Specifically, $R^1$ is —$CH_2C(=O)C_{1-4}$alkyl.

Specifically, $R^1$ is $CF_3$.

Specifically, $R^1$ is cyclopropyl.

Specifically, $R^2$ and $R^3$ are independently H or F.

Specifically, at least one of $R^2$ and $R^3$ is F.

Specifically, $R^2$ and $R^3$ are F.

Specifically, Y is S, SO, or $SO_2$.

Specifically, Y is S, or $SO_2$.

Specifically, Y is $S(=NR^8)$, or $S(=NR^8)(=O)$.

Specifically, X is N.

Specifically, X is CH.

Specifically, n is 1.

Specifically, $R^4$, $R^5$ and $R^6$ are H.

Specifically, Y is S, SO, or $SO_2$; and X is N or CH.

Specifically, $R^2$ and $R^3$ are independently H or F; and $R^4$, $R^5$, and $R^6$ are H.

Specifically, $het^1$ is isoxazolyl, 1,2,5-thiadiazolyl, or pyridyl.

Specifically, $het^2$ is 1,2,3-triazolyl.

Specific compounds of the present invention are those wherein structure i, ii, or iii has an optical configuration below:

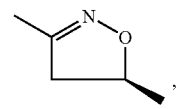

i

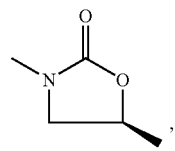

ii

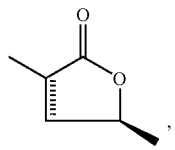

iii

It will be appreciated by those skilled in the art that compounds of the present invention may have additional chiral centers and be isolated in optically active and racemic forms. The present invention encompasses any racemic, optically-active, tautomeric, or stereoisomeric form, or mixture thereof, of a compound of the invention.

Another specific compounds of the present invention are the compounds of formula II

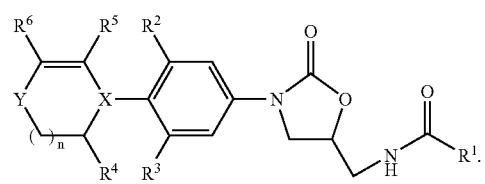

II

Another specific compounds of the present invention are the compounds of formula III

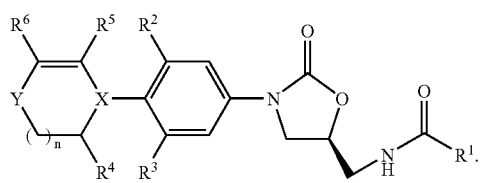

III

Another specific compounds of the present invention are the compounds of formula IV

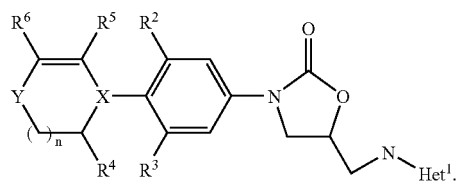

IV

Another specific compounds of the present invention are the compounds of formula V

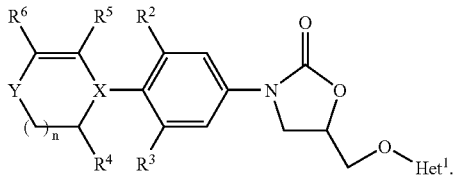

Another specific compounds of the present invention are the compounds of formula VI

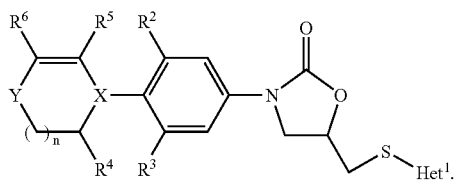

Another specific compounds of the present invention are the compounds of formula VII

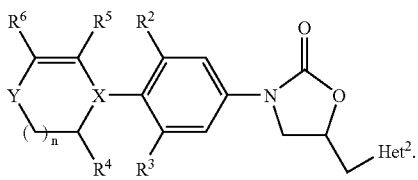

Examples of the present invention are:

N-[[(5S)-3-[4-(3,4-dihydro-2H-thiopyran-4-yl)-3-fluorophenyl]-2-oxo-5-oxazolidinyl]methyl]-2,2,2-trifluoroacetamide, N-[[(5S)-3-[4-(3,4-dihydro-2H-thiopyran-4-yl)-3-fluorophenyl]-2-oxo-5-oxazolidinyl]methyl]acetamide, N-[[(5S)-3-[4-(3,4-dihydro-2H-thiopyran-4-yl)-3-fluorophenyl]-2-oxo-5-oxazolidinyl]methyl]ethanethioamide, N-[[(5S)-3-[4-(3,4-dihydro-1-oxido-2H-thiopyran-4-yl)-3-fluorophenyl]-2-oxo-5-oxazolidinyl]methyl]acetamide, N-[[(5S)-3-[4-(3,4-dihydro-1,1-dioxido-2H-thiopyran-4-yl)-3-fluorophenyl]-2-oxo-5-oxazolidinyl]methyl]acetamide, N-[[(5S)-3-[4-(3,4-dihydro-1-oxido-2H-thiopyran-4-yl)-3-fluorophenyl]-2-oxo-5-oxazolidinyl]methyl]ethanethioamide, N-[[(5S)-3-[4-(2,3-dihydro-1,1-dioxido-4H-1,4-thiazin-4-yl)-3-fluorophenyl]-2oxo-5-oxazolidinyl]methyl]acetamide, N-[[(5S)-3-[4-(2,3-dihydro-1,1-dioxido-4H-1,4-thiazin-4-yl)-3,5-difluorophenyl]2-oxo-5-oxazolidinyl]methyl]acetamide, N-[[(5S)-3-[4-(3,4-dihydro-1,1-dioxido-2H-thiopyran-4-yl)-3-fluorophenyl]-2-oxo-5-oxazolidinyl]methyl]-2,2-difluoroacetamide, N-[[(5S)-3-[4-(3,4-dihydro-1,1-dioxido-2H-thiopyran-4-yl)-3-fluorophenyl]-2-oxo-5-oxazolidinyl]methyl]-2,2-difluoroethanethioamide, 2,2-Dichloro-N-[[(5S)-3-[4-(3,4-dihydro-1,1-dioxido-2H-thiopyran-4-yl)-3-fluorophenyl]-2-oxo-5-oxazolidinyl]methyl]acetamide, N-[[(5S)-3-[4-(3,4-dihydro-4-hydroxy-1,1-dioxido-2H-thiopyran-4-yl)-3-fluorophenyl]-2-oxo-5-oxazolidinyl]methyl]acetamide, N-[[(5S)-3-[3-Fluoro-4-(4-fluoro-3,4-dihydro-1,1-dioxido-2H-thiopyran-4-yl)phenyl]-2-oxo-5-oxazolidinyl]methyl]acetamide, N-[[(5S)-3-[4-(3,4-dihydro-1,1-dioxido-2H-thiopyran-4-yl)phenyl]-2-oxo-5-oxazolidinyl]methyl]acetamide, N-[[(5S)-3-[4-(3,4-dihydro-1,1-dioxido-2H-thiopyran-4-yl)phenyl]-2-oxo-5-oxazolidinyl]methyl]-2,2-difluoroacetamide, 2,2-dichloro-N-[[(5S)-3-[4-(3,4-dihydro-1,1-dioxido-2H-thiopyran-4-yl)phenyl]-2-oxo-5-oxazolidinyl]methyl]acetamide,

[[(5S)-3-[4-(3,4-dihydro-1,1-dioxido-2H-thiopyran-4-yl)phenyl]-2-oxo-5-oxazolidinyl]methyl]-2,2-difluoroethanethioamide, N-[[(5S)-3-[4-(3,4-dihydro-1,1-dioxido-2H-thiopyran-4-yl)phenyl]-2-oxo-5-oxazolidinyl]methyl]propionamide, (S)-[[3-[4-(3,4-dihydro-1,1-dioxido-2H-thiopyran-4-yl)phenyl]-2-oxo-5-oxazolidinyl]methyl]carbamic acid, methyl ester, N-[[(5S)-3-[4-(3,4-dihydro-1,1-dioxido-2H-thiopyran-4-yl)-3,5-difluorophenyl]-2-oxo-5-oxazolidinyl]methyl]acetamide, N-[[(5S)-3-[4-(2,3-dihydro-1,1-dioxido-4H-1,4-thiazin-4-yl)-3-fluorophenyl]-2oxo-5-oxazolidinyl]methyl]-2,2-difluoroethanethioamide, 2,2-dichloro-N-[[(5S)-3-[4-(2,3-dihydro-1,1-dioxido-4H-1,4-thiazin-4-yl)-3-fluorophenyl]-2-oxo-5-oxazolidinyl]methyl]acetamide, N-[[(5S)-3-[4-(2,3-dihydro-1,1-dioxido-4H-1,4-thiazin-4-yl)-3-fluorophenyl]-2-oxo-5-oxazolidinyl]methyl]-2,2-difluoroacetamide, N-[[(5S)-3-[4-(2,3-dihydro-1,1-dioxido-4H-1,4-thiazin-4-yl)phenyl]-2-oxo-5-oxazolidinyl]methyl]-2,2-difluoroethanethioamide, 2,2-dichloro-N-[[(5S)-3-[4-(2,3-dihydro-1,1-dioxido-4H-1,4-thiazin-4-yl)phenyl]2-oxo-5-oxazolidinyl]methyl]acetamide, N-[[(5S)-3-[4-(2,3-dihydro-1,1-dioxido-4H-1,4-thiazin-4-yl)phenyl]-2-oxo-5-oxazolidinyl]methyl]-2,2-difluoroacetamide, N-[[(5S)-3-[4-(2,3-Dihydro-1,1-dioxido-4H-1,4-thiazin-4-yl)-3,5-difluorophenyl]2-oxo-5-oxazolidinyl]methyl]-2,2-difluoroethanethioamide, 2,2-dichloro-N-[[(5S)-3-[4-(2,3-dihydro-1,1-dioxido-4H-1,4-thiazin-4-yl)-3,5-difluorophenyl]-2-oxo-5-oxazolidinyl]methyl]acetamide, or N-[[(5S)-3-[4-(2,3-dihydro-1,1-dioxido-4H-1,4-thiazin-4-yl)-3,5-difluorophenyl]2-oxo-5-oxazolidinyl]methyl]-2,2-difluoroacetamide.

The following Schemes describe the preparation of compounds of the present invention. All of the starting materials are prepared by procedures described in these schemes or by procedures that would be well known to one of ordinary skill in organic chemistry. The variables used in the Schemes are as defined below or as in the claims.

The compounds of this invention can be prepared in accordance to one or more of the Schemes discussed below.

Optically pure material could be obtained either by one of a number of asymmetric syntheses or alternatively by resolution from a racemic mixture.

As shown in Scheme I, dihydrothiopyran and dihydrothiazine compounds can be made by Pummerer-type reactions of thiopyran and thiomorpholine S-oxide (sulfoxide) derivatives. This transformation of alkyl sulfoxides into the respective alpha, beta-unsaturated sulfide compounds is well known by one skilled in the art. For example, the reaction of a sulfoxide compound with an acetic anhydride is described by Schlessinger et al. in J. Am. Chem. Soc., 1967, vol. 89, p. 7138. Optionally, transformations of this type are performed with a carboxylic acid anhydride in the presence of an acid (e.g., Monteiro et al., Synthesis, 1975, p. 437) or base compounds (Kim et al., J. Org. Chem., 1982, vol. 47, p. 170). Also optionally, such syntheses are conducted with a carboxylic acid anhydride under thermal conditions as described by Mikolajczyk in Tetrahedron, 1983, vol. 39, p. 1189. The preparation of alpha,beta-unsaturated sulfide compounds from alkyl sulfoxides can also be achieved utilizing protic acids (see, e.g., Yamamoto et al., Angew. Chem., Int. Ed. Engl., 1986, vol. 25, p. 635). These syntheses are also performed with a Lewis acid, such as trimethylsilyl triflate (e.g., Bushweller et al., J. Org. Chem., 1989, vol. 54, p. 2404) or trimethylsilyl halide (see, e.g., Schaumann et al., Synthesis, 1990, p. 271) in the presence of a base, such as N,N,N-diisopropylethylamine or lithium N,N-diisopropylamide. It is understood that a variation or combination of these methods may be employed in the synthesis of the novel dihydrothiopyran and dihydrothiazine compounds described in the present application.

Scheme I below serves to illustrate one general synthesis of dihydrothiopyran derivatives bearing an oxazolidinone group. Starting thiopyran sulfoxide compounds are prepared as described in International Publication WO 98/54161, published 3 Dec. 1998. In step 1 of this synthesis, a suitable thiopyran sulfoxide derivative is converted into a dihydrothiopyran by Pummerer transformation with an acylating agent, such as trifluoroacetic anhydride, acetic anhydride, or an acyl chloride reagent such as acetyl chloride, in the presence of an optional organic or inorganic basic agent, such as pyridine, triethylamine, or potassium carbonate. These transformations are generally performed at 0° C. to 50° C. using aprotic organic solvents, such as acetonitrile, dimethylformamide, tetrahydrofuran, and dichloromethane. Optionally, the synthesis can be performed at an elevated temperature (typically at 70–130° C.) in the absence of base.

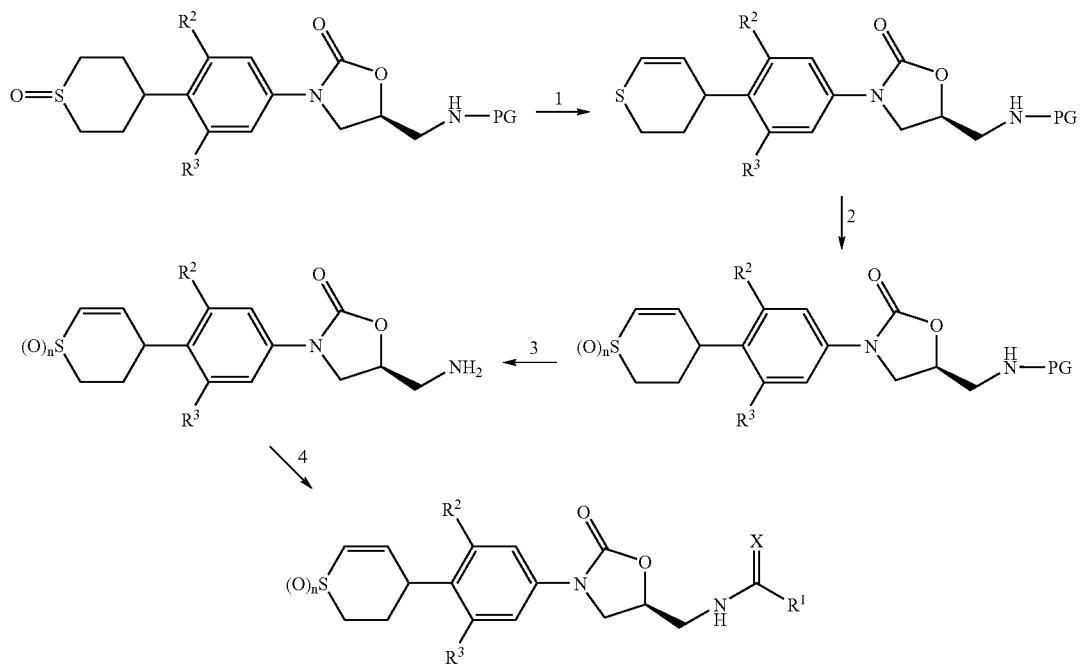

SCHEME I

Step 2 of the Scheme I involves an optional oxidation of the dihydrothiopyran intermediate en route to a dihydrothiopyran sulfoxide or dihydrothiopyran sulfone compound, as needed (n=1 or 2). Oxidation into sulfoxide (n=1) can be effected with an inorganic oxidant such as sodium periodate or ceric ammonium nitrate (CAN) in a polar organic solvent, such as methanol or acetonitrile, with optional addition of water. This transformation is normally conducted at temperatures in a range of from about 0° C. to about 40° C. Oxidation into the sulfone derivative (n=2) can be achieved using meta-chloroperoxybenzoic acid (MCPBA). This reaction is commonly performed in organic solvents, such as dichloromethane, dichloroethane, or methanol, at a temperature in a range of from about 10° C. to about 60° C. Optionally, the latter conversion can also be performed with hydrogen peroxide solutions in presence of methyl trioxorhenium catalyst (MTO).

Step 3 of the Scheme I involves an optional deprotection of an oxazolidinone intermediate wherein PG is a protective group, such as tert-butyloxycarbonyl (Boc). It is convenient to remove the Boc group with hydrogen chloride in dioxane at a temperature in a range of from about 0° C. to about 24° C.; however, other deprotection strategies can be employed.

The synthesis of Scheme I is then completed by an acylation or thioacylation of the penultimate amine intermediate using known art. Thus, acylations can be routinely performed by reaction of the amine with carboxylic acid anhydrides or esters. These transformations are generally performed at a temperature in a range of from about 0° C. to about 50° C. using polar solvents, such as acetonitrile, dimethylformamide, tetrahydrofuran, and methanol or mixtures thereof with optional apolar solvents, such as dichloromethane. These reactions are preferably conducted in the presence of an organic or inorganic base, such as pyridine, triethylamine, or potassium carbonate. Thioacylations are accomplished by allowing amine intermediates to react with dithioesters or thionoesters and a tertiary amine base such as triethylamine. In this reaction, it is often convenient to employ an excess of the tertiary amine base with an amine salt prepared by Boc deprotection in step 2 without first isolating the free base. Solvents such as tetrahydrofuran, methylene chloride or preferably methanol, and at a temperature in the range of from bout 24° C. to about 50° C. can be used for this reaction. Other thiocarbonyl compounds of the Scheme I can be prepared according to the procedures disclosed in PCT International Publication WO 98/54161.

Alternatively, dihydrothiopyran compounds can be synthesized from 5(S)-aminomethyloxazolidinone thiopyran S-oxide derivatives (prepared as described in International Publication WO 98/54161, published 3 Dec. 1998), as illustrated in Scheme II. In the first step of the Scheme II, the Pummerer-type conversion of the thiopyran sulfoxide into a dihydrothiopyran heterocycle takes place concomitantly with the acylation of the aminomethyl group. Reaction conditions for this transformation are essentially identical to that employed in the step 1 of Scheme I.

Step 2 of the Scheme II involves an optional deprotection of the 5-amidomethyl group when further variations at this position are desired. In one preferred embodiment, R is a trifluoromethyl group resulting from use of trifluoroacetic anhydride in the step 1 of Scheme II. This group can be readily removed using an inorganic base such as potassium or lithium carbonate, in a polar organic solvent, such as methanol or dioxane, with an optional addition of water. The transformation is typically performed at a temperature in a range of from about 24° C. to about 50° C. The synthesis is then completed by performing acylation or thioacylation and optional oxidation steps (n=1 or 2) as described in Scheme I.

SCHEME II

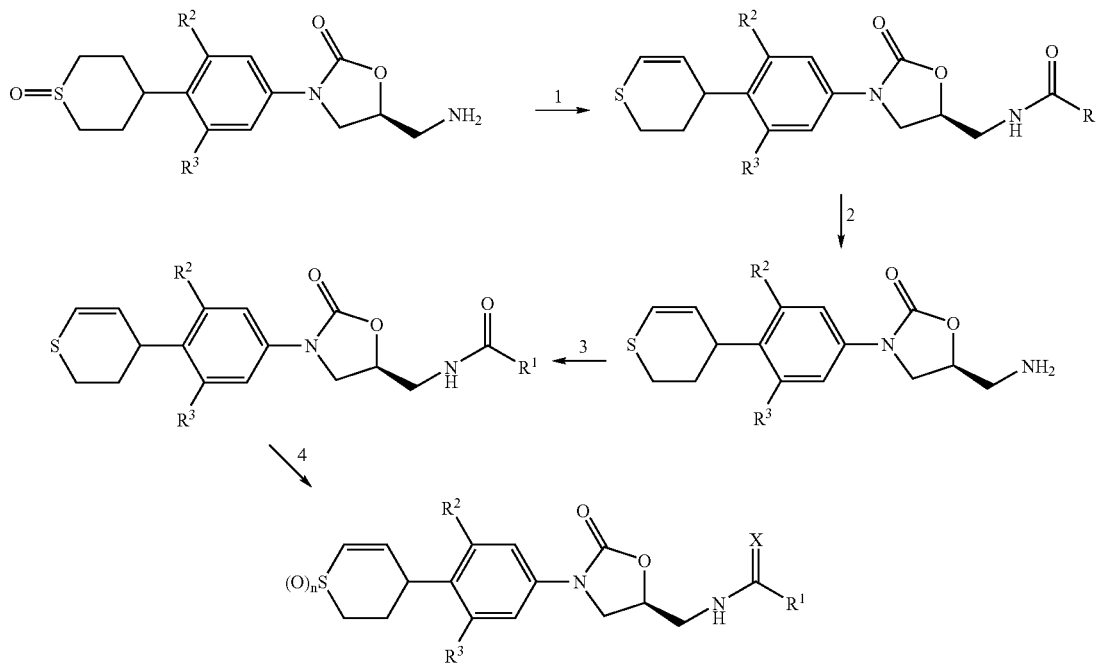

Scheme III serves to illustrate one general synthesis of dihydrothiazine compounds from thiomorpholine S-oxide oxazolidinone compounds (prepared as described as described in International Publication WO 95/07271, published on 16 Mar. 1995). Step 1 of this synthesis is essentially performed under conditions essentially identical to that employed in the method of Scheme 1. One difference between the syntheses of Schemes I and III is that the Pummerer-type conversion of thiomorpholine compounds can be accompanied by a concomitant C-acylation of the dihydrothiazine intermediate by an acylating reagent (see Scheme III, wherein R' can be COCF$_3$, among the other acylating reagents).

Step 2 of the synthesis of Scheme DI involves an oxidation of the dihydrothiazine intermediate under conditions described in step 2 of Scheme I. Step 3 of involves an optional deacylation of the 2-acyldihydrothiazine intermediate. This reaction is performed in a polar organic solvent, such as methanol or dimethylformamide, in presence of inorganic base, such as potassium carbonate or lithium hydroxide. The transformation is typically performed at a temperature in a reange of from about 40° to about 100° C.

SCHEME III

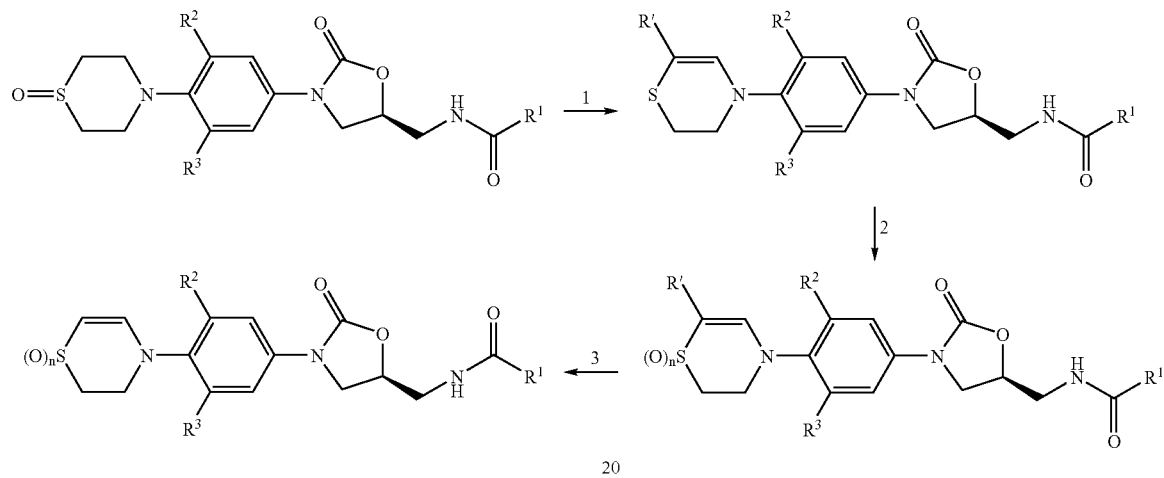

Alternatively, dihydrothiazine compounds can be prepared as shown in Scheme IV by dehydrogenation of thiomorpholine S,S-dioxides (prepared as described in the International Publication WO 95/07271, published on 16 Mar. 1995). The transformation can be effected with a suitable organic oxidant, such as 2,3-dichloro-5,6-dicyanobenzoquinone (DDQ) or chloroanil. The transformation is typically performed in a polar organic solvent, such as dioxane, tetrahydrofuran, or dimethylacetamide; at a temperature range of about 60° C. to about 110° C.

SCHEME IV

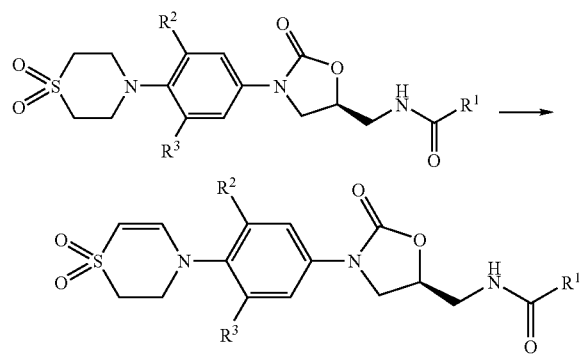

In another variation of the synthesis of Scheme IV, the dihydrothiazine S,S-dioxide heterocycle can be synthesized prior to the oxazolidinone ring construction as shown in Scheme V. In the first step of Scheme V, suitable thiomorpholine-substituted anilines (prepared as described in the International Publication WO 95/07271, published on 16 Mar. 1995) are reacted with an alkyl chloroformate reagent, such as isobutyl chloroformate in the presence of an organic or inorganic base, such as pyridine, triethylamine, or potassium carbonate. The reaction is typically performed in aprotic organic solvent, such as tetrahydrofuran, dioxane, or acetonitrile, at a temperaure in a range of from about −5° C. to about 25° C.

The resulting aryl carbamate thiomorpholine intermediates are oxidized into the corresponding thiomorpholine S,S-dioxide compounds as shown in step 2 of the Scheme V. This conversion is commonly performed with meta-chloroperoxybenzoic acid (MCPBA) in organic solvent such as dichloromethane, at a temperature in a range of from about 0° C. to about 30° C.

Step 3 of the Scheme V involves dehydrogenation of a thiomorpholine S,S-dioxide compound into a dihydrothiazine S,S-dioxide intermediate. This reaction is conducted under the similar conditions as described in Scheme IV.

Step 4 illustrates a construction of the oxazolidinone group. Transformations of aryl carbamates into oxazolidinone are known to those skilled in the art (see, e.g., International Publication WO 95/07271, published on 16 Mar. 1995). In step 4 the synthesis is performed with (3-chloro-2-hydroxy-propyl)-carbamic acid tert-butyl ester (prepared according to the procedure described in U.S. patent application Ser. No. 09/982,157) to afford the Boc-protected oxazolidinone intermediate. The reaction is performed in the presence of an organic base, such as lithium tert-butoxide, in a polar organic solvent such as dimethylformamide, at a temperature of about −5° C. to about 25° C.

The resulting Boc-protected intermediates are then deprotected with a trialkylsilyl halide or triflate, such as trimethylsilyl triflate (TMSOTf) in the presence of an organic base, such as lutidine. This reaction is preferably performed in an organic solvent, such as dichloromethane, at a temperature of about 0° C. to about 40° C. The synthesis is then completed by acylation or thioacylation of the amine intermediate as described in step 3 of Scheme II.

SCHEME V

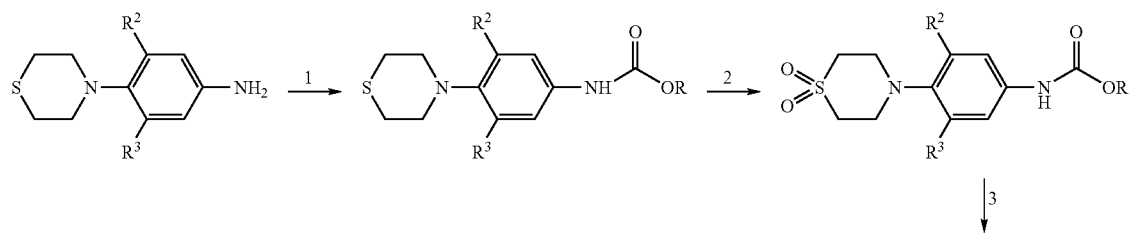

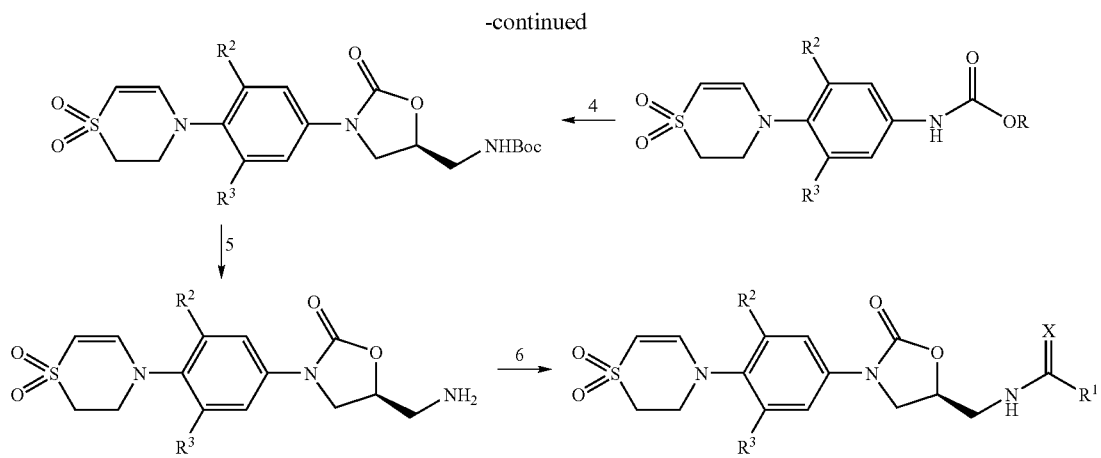

Salts

The compound of formula I may be used in its native form or as a salt. In cases where forming a stable nontoxic salt is desired, administration of the compound as a pharmaceutically acceptable salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, ketoglutarate, and glycerophosphate. Suitable inorganic salts may also be formed, including hydrochloride, hydrobromide, sulfate, nitrate, bicarbonate, and carbonate salts.

Pharmaceutically acceptable salts may be obtained using standard procedures well known in the art, for example by reacting a compound of the present invention with a suitable acid affording a physiologically acceptable anion.

Routes of Administration

The oxazolidinone antibacterial agents of this invention have useful activity against a variety of organisms including, but not limiting to, *Staphylococcus aureus, Staphylococcus epidennidis, Enterococcus faecium, Streptococcus pneumoniae, Streptococcus pyogenes, Enterococcus faecalis, Moraxella catarrhalis* and *H. influenzae*. In therapeutic use for treating, or combating, bacterial infections in a mammal (i.e. human and animals) a compound of the present invention or its pharmaceutical compositions can be administered orally, parenterally, topically, rectally, transmucosally, or intestinally.

Parenteral administrations include indirect injections to generate a systemic effect or direct injections to the afflicted area. Examples of parenteral administrations are subcutaneous, intravenous, intramuscular, intradermal, intrathecal, intraocular, intranasal, intravetricular injections or infusions techniques.

Topical administrations include the treatment of infectious areas or organs readily accessibly by local application, such as, for example, eyes, ears including external and middle ear infections, vaginal, open wound, skins including the surface skin and the underneath dermal structures, or other lower intestinal tract. It also includes transdermal delivery to generate a systemic effect.

The rectal administration includes the form of suppositories.

The transmucosal administration includes nasal aerosol or inhalation applications.

The preferred routes of administration are oral and parenteral.

Composition/Formulation

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, solutions, emulsions, gels, syrups, slurries, suspensions and the like, for oral ingestion by a patient. A carrier can be at least one substance which may also function as a diluent, flavoring agent, solubilizer, lubricant, suspending agent, binder, tablet disintegrating agent, and encapsulating agent. Examples of such carriers or excipients include, but are not limited to, magnesium carbonate, magnesium stearate, talc, sugar, lactose, sucrose, pectin, dextrin, mannitol, sorbitol, starches, gelatin, cellulosic materials, low melting wax, cocoa butter or powder, polymers such as polyethylene glycols and other pharmaceutical acceptable materials.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono-, di- or triglycerides. Stabilizers may be added in these formulations, also.

Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

The compounds may also be formulated for parenteral administration, e.g., by injections, bolus injection or continuous infusion. Formulations for parenteral administration may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

For injection, the compounds of the invention may be formulated in aqueous solution, preferably in physiologically compatible buffers or physiological saline buffer. Suitable buffering agents include trisodium orthophosphate, sodium bicarbonate, sodium citrate, N-methylglucamine, L(+)-lysine and L(+)-arginine.

Parenteral administrations also include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use. For suppository administration, the compounds may also be formulated by mixing the agent with a suitable non-irritating excipient which is solid at room temperature but liquid at rectal temperature and therefore will melt in the rectum to release the drug. Such materials include cocoa butter, beeswax and other glycerides.

For administration by inhalation, compounds of the present invention can be conveniently delivered through an aerosol spray in the form of solution, dry powder, or suspensions. The aerosol may use a pressurized pack or a nebulizer and a suitable propellant. In the case of a pressurized aerosol, the dosage unit may be controlled by providing a valve to deliver a metered amount. Capsules and cartridges of, for example, gelatin for use in an inhaler may be formulated containing a power base such as lactose or starch.

For topical applications, the pharmaceutical composition may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion such as suspensions, emulsion, or cream containing the active components suspended or dissolved in one or more pharmaceutically acceptable carriers. Suitable carriers include, but are not limited to, mineral oil, sorbitan monostearate, polysorbate 60, cetyl esters wax, ceteary alcohol, 2-octyldodecanol, benzyl alcohol and water.

For ophthalmic and otitis uses, the pharmaceutical compositions may be formulated as micronized suspensions in isotonic, pH adjusted sterile saline, or preferably, as solutions in isotonic, pH adjusted sterile saline, either with or without a preservative such as a benzylalkonium chloride. Alternatively, for ophthalmic uses, the pharmaceutical compositions may be formulated in an ointment such as petrolatum.

In addition to the formulations described previously, the compounds may also be formulated as depot preparations. Such long acting formulations may be in the form of implants. A compound of this invention may be formulated for this route of administration with suitable polymers, hydrophobic materials, or as a sparing soluble derivative such as, without limitation, a sparingly soluble salt.

Additionally, the compounds may be delivered using a sustained-release system. Various sustained-release materials have been established and are well known by those skilled in the art. Sustained-release capsules may, depending on their chemical nature, release the compounds for 24 hours or for up to several days.

Dosage

Pharmaceutical compositions suitable for use in the present invention include compositions wherein the active ingredients are contained in an amount sufficient to achieve the intended purpose, i.e., the treatment or prevent of infectious diseases. More specifically, a therapeutically effective amount means an amount of compound effective to prevent, alleviate or ameliorate symptoms of disease or prolong the survival of the subject being treated.

The quantity of active component, that is the compound of this invention, in the pharmaceutical composition and unit dosage form thereof may be varied or adjusted widely depending upon the manner of administration, the potency of the particular compound and the desired concentration. Determination of a therapeutically effective amount is well within the capability of those skilled in the art. Generally, the quantity of active component will range between 0.5% to 90% by weight of the composition.

Generally, an antibacterially effective amount of dosage of active component will be in the range of about 0.1 to about 400 mg/kg of body weight/day, more preferably about 1.0 to about 50 mg/kg of body weight/day. It is to be understood that the dosages may vary depending upon the requirements of each subject and the severity of the bacterial infection being treated. In average, the effective amount of active component is about 200 mg to 800 mg and preferable 600 mg per day.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

In cases of local administration or selective uptake, the effective local concentration of the drug may not be related to plasma concentration and other procedures know in the art may be used to determine the desired dosage amount.

Compounds of this invention have useful activity against a variety of organisms. The in vitro activity of compounds of this invention can be assessed by standard testing procedures such as the determination of minimum inhibitory concentration (MIC) by agar dilution as described in "Approved Standard. Methods for Dilution Antimicrobial Susceptibility Tests for Bacteria That Grow Aerobically", 3rd. ed., published 1993 by the National Committee for Clinical Laboratory Standards, Villanova, Pa., USA. The activity of compounds of this invention against *Staphylococcus aureus* UC9213 (S.A.) is shown in Table 1.

TABLE 1

| Antibacterial Activity, Minimum Inhibitory Concentration (MIC µg/mL) | |
|---|---|
| EXAMPLES | SPNE 9912 |
| 1 | 2 |
| 2 | 1 |
| 3 | 0.5 |
| 4 | 1 |
| 5 | 0.25 |
| 6 | 0.25 |
| 7 | 0.5 |
| 8 | 0.5 |
| 9 | 0.5 |
| 10 | 0.25 |
| 11 | 0.5 |
| 12 | — |
| 13 | — |
| 14 | 1 |
| 15 | 0.5 |
| 16 | 0.25 |
| 17 | 0.25 |
| 18 | 1 |
| 19 | 2 |
| 20 | 1 |
| 21 | 0.25 |
| 22 | 0.25 |
| 23 | 0.5 |
| 24 | 0.5 |
| 25 | 1 |
| 26 | 1 |
| 27 | 0.25 |
| 28 | 0.5 |
| 29 | 0.5 |
| 30 | 1 |
| 31 | 0.5 |
| 32 | 0.5 |

Minimum inhibitory concentration (MIC) refers to lowest concentration of drug (µg/mL) that inhibits visible growth of the organism. "--" refers to the activity data is not available.

EXAMPLES

Example 1

Preparation of N-[[(5S)-3-[4-(3,4-dihydro-2H-thiopyran-4-yl)-3-fluorophenyl]-2-oxo-5-oxazolidinyl]methyl]-2,2,2-trifluoroacetamide

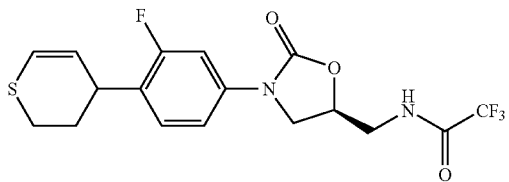

Trifluoroacetic anhydride (0.63 g, 3.0 mmol) is added dropwise with stirring to a solution of (5S)-5-(aminomethyl)-3-[3-fluoro-4-(tetrahydro-1-oxido-2H-thiopyran-4-yl)phenyl]-2-oxazolidinone (0.326 g, 1.0 mmol; prepared as described in U.S. Pat. No. 5,968,962) and 4-methylmorpholine (0.808 g, 8.0 mmol) in DCM (20 mL) at ca. 0° C. under nitrogen atmosphere. The mixture is allowed to warm up to r.t. and stirred for another 5 h. Solvent is removed under vacuum and the crude product is purified by silica gel column chromatography (eluent EtOAC—hexanes 1:1).

MS (m/z): 405 [M+H]+. 1H NMR (300 MHz, DMSO-d6): 1.82–1.97 (m, 1H), 2.04–2.19 (m, 1 H), 2.65–2.78 (m, 1H), 2.88–3.00 (m, 1 H), 3.54–3.60 (m, 2 H), 3.75–4.84 (m, 2 H), 4.18 (t, J=9.3 Hz, 1H), 4.80 (m, 1H), 5.67 (dd, J=10.2 and 3.9 Hz, 1H), 6.20 (d, J=10.2 Hz, 1H), 7.16–7.28 (m, 2H), 7.48 (m, 1H), 9.80 (br. s, 1H).

Example 2

Preparation of N-[[(5S)-3-[4-(3,4-dihydro-2H-thiopyran-4-yl)-3-fluorophenyl]-2-oxo-5-oxazolidinyl]methyl]acetamide

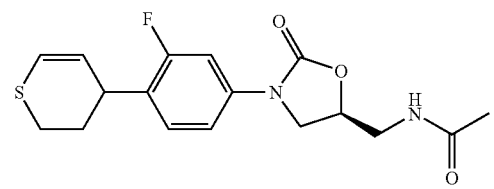

Method A. Step 1. 1 M aq. K2CO3 (5.0 mL) is added to the product of Example 1 (0.404 g, 1.0 mmol) in MeOH (5.0 mL), and the mixture is stirred at r.t. for 3 h. Solvent is removed under vacuum.

Step 2. Half of the crude intermediate amine prepared in Step 1 (ca 0.5 mmol) is dissolved in DMF (2.0 mL). Pyridine (5 mmol) and acetic anhydride (5 mmol) are added, and the mixture is stirred for 1 h. Most of solvent is removed under vacuum, and the product purified by RP HPLC.

MS (m/z): 351 [M+H]+. 1H NMR (300 MHz, DMSO-d6): 1.80 (s, 3 H), 1.90 (m, 1 H), 2.14 (m, 1H), 2.70 (m, 1 H), 2.92 (m, 1 H), 3.40 (m, 2 H), 3.65–4.13 (m, 3 H), 4.72 (m, 1H), 5.65 (dd, J=10.2 and 3.9 Hz, 1H), 6.40 (d, J=10.2 Hz, 1H), 7.19–7.26 (m, 2H), 7.48 (m, 1H), 8.22 (t, J=5.7 Hz, 1H).

Method B. 1 M Aq. K2CO3 (2 mL) is added to a solution of the product of Example 1 (1 mmol, 0.404 g) in MeOH (10 mL; to total ca. 0.17 M K2CO3 in MeOH—water 5:1). The solution is kept at r.t. for 3 h. Acetic anhydride (0.200 mL, 2.1 mmol) is added, and the mixture is stirred for 10 min. Acetic acid (0.100 mL) is added, and most of the solvent is removed under vacuum. The residue is distributed between EtOAc (40 mL) and water (20 mL), the organic layer is washed with water (2×30 mL), 2.5% aq. NaHCO3 (20 mL), water (30 mL), brine (30 mL), and dried (MgSO4). Solvent is removed under vacuum and residue is dried under high vacuum.

MS (m/z): 351 [M+H]+. 1H NMR (300 MHz, DMSO-d6): 1.80 (s, 3 H), 1.90 (m, 1 H), 2.14 (m, 1H), 2.70 (m, 1 H), 2.92 (m, 1 H), 3.40 (m, 2 H), 3.65–4.13 (m, 3 H), 4.72 (m, 1H), 5.65 (dd, J=10.2 and 3.9 Hz, 1H), 6.40 (d, J=10.2 Hz, 1H), 7.19–7.26 (m, 2H), 7.48 (m, 1H), 8.22 (t, J=5.7 Hz, 1H).

Example 3

Preparation of N-[[(5S)-3-[4-(3,4-dihydro-2H-thiopyran-4-yl)-3-fluorophenyl]-2-oxo-5-oxazolidinyl]methyl]ethanethioamide

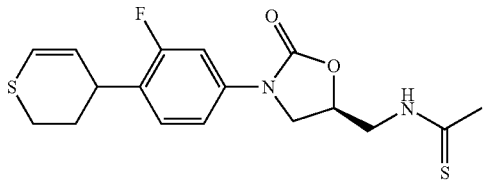

The crude amine from Example 2, Method A, Step 1 (ca 0.5 mmol) is dissolved in DMF (2.0 mL). Triethylamine (2 mmol) and ethyl dithioacetate (2 mmol) are added, and the mixture is stirred for 1 h. Most of solvent is removed under vacuum, and the product purified by RP HPLC.

MS (m/z): 367 [M+H]$^+$. $^1$H NMR (300 MHz, DMSO-d$_6$): 1.93 (m, 1 H), 2.13 (m, 1H), 2.44 (s, 3 H), 2.73 (m, 1 H), 2.91 (m, 1 H), 3.79–3.88 (m, 2 H), 3.91 (m, 2H), 4.16 (t, J=9.3 Hz, 1H), 4.95 (m, 1H), 5.69 (dd, J=10.2 and 3.9 Hz, 1H), 6.40 (d, J=10.2 Hz, 1H), 7.19–7.28 (m, 2H), 7.51 (m, 1H), 10.38 (br.s, 1H).

Example 4

Preparation of N-[[(5S)-3-[4-(3,4-dihydro-1-oxido-2H-thiopyran-4-yl)-3-fluorophenyl]-2-oxo-5-oxazolidinyl]methyl]acetamide

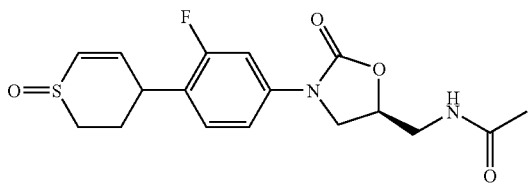

Meta-chloroperbenzoic acid (0.078 g, 0.45 mmol) is added with stirring to the amine from Example 2, Method A, Step 1 (175 mg, 0.5 mmol) in dichloromethane (2.0 mL). The mixture is stirred for 1 h. Solvent is removed under vacuum, and the crude product purified by preparative RP HPLC.

MS (m/z): 367 [M+H]$^+$. 1H NMR (300 MHz, DMSO-d$_6$; major diastereomer): 1.83 (s, 3H), 1.95–2.19 (m, 2H), 2.94–3.00 (m, 2H), 3.39–3.50 (m, 2 H), 3.70–3.81 (m, 2H), 4.12 (t, J=9.3 Hz, 1H), 4.74 (m, 1H), 6.42 (dd, J=10.5 and 2.1 Hz, 1H), 6.86 (dd, J=10.5 and 2.1 Hz, 1H), 7.20–7.30 (m, 2H), 7.54 (dd, J=13.2 and 2.1 Hz, 1H), 8.24 (t, J=5.7 Hz, 1H).

Example 5

Preparation of N-[[(5S)-3-[4-(3,4-Dihydro-1,1-dioxido-2H-thiopyran-4-yl)-3-fluorophenyl]-2-oxo-5-oxazolidinyl]methyl]acetamide

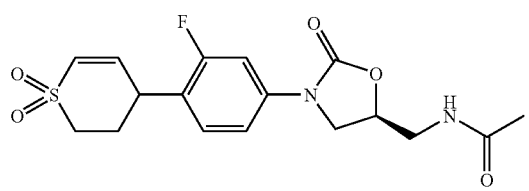

30% Aqueous H$_2$O$_2$ (0.034 mL, 0.3 mmol) is added to a solution of the amine from Example 2, Method A, Step 1 (0.07 g, 0.2 mmol) in DCM (1.0 mL) with pyridine (0.002 mL) and methyltrioxorhenium (0.001 g, MTO). The mixture is stirred at r.t. about 2 h. Solvent is removed under vacuum, and the crude product is purified by preparative RP HPLC.

MS (m/z): 383 [M+H]$^+$. 1H NMR (300 MHz, DMSO-d$_6$): 1.82 (s, 3H), 2.17–2.28 (m, 1H), 2.38–2.42 (m, 1H), 3.22–3.48 (m, 4 H), 3.72 (dd, J=6.6 and 8.5 Hz, 1H), 4.00–4.03 (m, 1H), 4.10 (dd, J=8.5 and 9.1 Hz, 1H), 4.70–4.75 (m, 1H), 6.45 (m, 1H), 6.78 (m, 1H), 7.20 (t, J=8.5 Hz, 1H), 7.29 (dt, J=1.9 and 8.5 Hz, 1H), 7.53 (dd, J=2.2 and 13.2 Hz, 1H), 8.23 (t, J=5.8 Hz, 1H).

Example 6

Preparation of N-[[(5S)-3-[4-(3,4-dihydro-1-oxido-2H-thiopyran-4-yl)-3-fluorophenyl]-2-oxo-5-oxazolidinyl]methyl]ethanethioamide

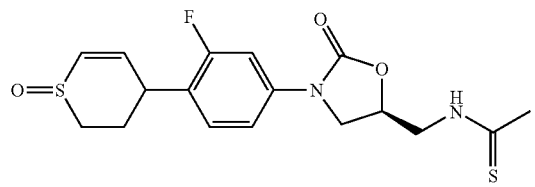

Step 1. The crude amine from Example 2, Method A, Step 1 (ca 0.5 mmol) is dissolved in DCM (3.0 mL). MCPBA (0.078 g, 0.45 mmol) is added, and the mixture is stirred for 2 h. The reaction mixture is then flushed through an ion exchange column Elut SCX (by Varian). The column is washed intermittently with excess of MeOH and water, and the intermediate sulfoxide is eluted with an excess of 0.7 M NH$_3$ in MeOH. Solvent is removed under vacuum, and the resulting solid is dried under high vacuum.

Step 2. A portion of the intermediate prepared in Step 1 (0.032 g, ca. 0.1 mmol) is dissolved in DMF (2.0 mL). Triethylamine (0.02 mL, 0.2 mmol) and ethyl dithioacetate (0.012 g, 0.1 mmol) are added, and the mixture stirred for 1 h. Solvent is removed under vacuum, and the crude product purified by preparative RP HPLC.

MS (m/z): 383 [M+H]$^+$. $^1$H NMR (300 MHz, DMSO-d$_6$; two diastereomers in a ratio ca. 1.5:1): 1.78–2.40 (m, 2H), 2.44 (s, 3 H), 2.86–3.20 (m, 2H), 3.70–4.00 (m, 4H), 3.99–4.21 (m, 1 H), 4.96 (m, 1H), 6.31 (dd, J=10.2 and 3.9 Hz, 0.4H, minor diastereomer), 6.43 (dd, J=10.5 and 2.7 Hz, 0.6H, major diastereomer), 6.73 (d, J=10.2 Hz, 0.4H, minor diastereomer), 6.86 (d, J=10.5 Hz, 0.6 H, major diastereomer), 7.13 (dd, J=8.7 and 8.3 Hz, 0.4 H, minor diastereomer), 7.16–7.58 (m, 2.6 H), 10.38 (br.s, 1H).

Example 7

Preparation of N-[[(5S)-3-[4-(2,3-dihydro-1,1-dioxido-4H-1,4-thiazin-4-yl)-3-fluorophenyl]-2-oxo-5-oxazolidinyl]methyl]acetamide

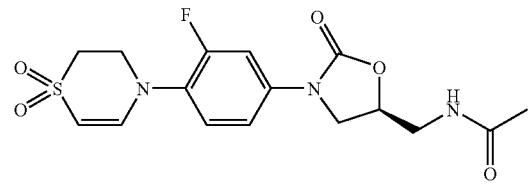

Step 1. Preparation of N-[[(5S)-3-[4-[2,3-dihydro-6-(trifluoroacetyl)-4H-1,4-thiazin-4--yl]-3,5-difluorophenyl]-2-oxo-5-oxazolidinyl]methyl]acetamide.

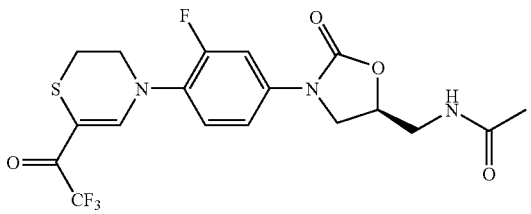

4-Methylmorpholine (1.2 mL, 11.1 mmol) is added to a solution of N-[[(5S)-3-[3-fluoro-4-(1-oxido-4-thiomorpholinyl)phenyl]-2-oxo-5-oxazolidinyl]methyl]acetamide (0.690 g, 1.87 mmol; prepared as described in U.S. Pat. No. 5,688,792) in DCM (40 mL), followed by trifluoroacetic anhydride (1.06 mL, 7.5 mmol). The solution is stirred at r.t. for about 20 h, and is concentrated under vacuum, then dissolved in 100 mL of EtOAc—2.5% aq. NaHCO₃ (1:1). Aqueous phase is extracted with EtOAc (2×50 mL). The combined organic layers are washed with brine, and dried (MgSO₄). Solvent is removed under vacuum to afford the title compound that is used directly without further purification.

Step 2: Preparation of N-[[(5S)-3-[4-[2,3-dihydro-1,1-dioxido-6-(trifluoroacetyl)-4H-1,4-thiazin-4-yl]-3-fluorophenyl]-2-oxo-5-oxazolidinyl]methyl]acetamide.

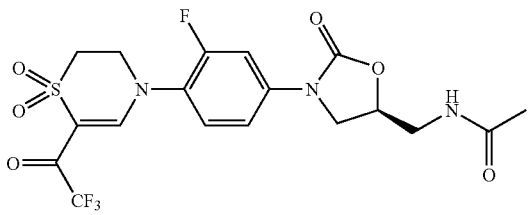

The product of Step 1 (0.836 g, 1.87 mmol) is dissolved in DCM (50 mL), and the solution cooled down to 0° C. m-Chloroperoxybenzoic acid (1.072 g of the 60% Aldrich material, 3.74 mmol) is added, and the mixture is stirred at r.t. for about 2 h. Additional m-chloroperoxybenzoic acid (0.25 g of a 60% mixture, 0.94 mmol) is added, and the mixture stirred for another 1 h. Saturated aq. Na₂S₂O₃ (2 mL), 50 mL of 2.5% aq. NaHCO₃ (50 mL) are added. The layers are separated, and the aq. phase extracted with DCM (2×50 mL). The combined organic phases are washed with saturated NaHCO₃, brine, and dried (MgSO₄). The solvent is removed under vacuum to afford the title compound.

Step 3. Preparation of N-[[(5S)-3-[4-(2,3-dihydro-1,1-dioxido-4H-1,4-thiazin-4yl)-3-fluorophenyl]-2-oxo-5-oxazolidinyl]methyl]acetamide.

The product of Step 2 (0.670 g, 1.39 mmol) is suspended in 28 mL of methanol, and the solution heated to reflux. Dry K₂CO₃ (0.386 g, 2.8 mmol) is added, and the mixture is stirred at reflux for 1 h. Upon cooling, the solution is diluted with 2.5% aq. NaHCO₃ (20 mL) and the methanol removed by rotary evaporation. The resulting aqueous phase is extracted with EtOAc (5×30 mL), and the combined organic layers are dried (MgSO₄). Solvent is evaporated under vacuum, and the crude material purified by silica gel column chromatography (gradient 0–4% MeOH-DCM) to afford the title compound as a white solid. Yiled 0.309 g (58%). R_f=0.13 (5% MeOH-DCM). M.p. 193°–194° C.

MS (m/z): [M+H]⁺=384. ¹H NMR (300 MHz, CD₃OD): 1.95 (s, 3H), 3.35–3.37 (m, 2H), 3.54–3.56 (m, 2H), 3.78–3.84 (m, 1H), 4.11–4.26 (m, 3H), 4.77–4.82 (m, 1H), 5.38 (d, J=9 Hz, 1H), 6.94 (d, J=9 Hz, 1H), 7.29–7.38 (m, 2H), 7.65 (dd, J=2 and 14 Hz, 1H).

Example 8

Preparation of N-[[(5S)-3-[4-(2,3-dihydro-1,1-dioxido-4H-1,4-thiazin-4-yl)-3,5-difluorophenyl]-2-oxo-5-oxazolidinyl]methyl]acetamide

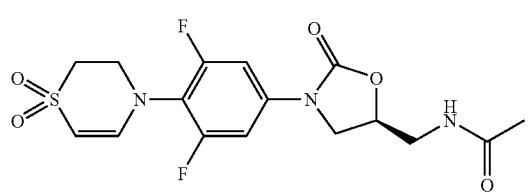

Step 1. Preparation of isobutyl 4-(1,1-dioxido-2,3-dihydro-4-thiazinyl)-3,5-difluorophenylcarbamate.

A solution of isobutyl 4-(1,1-dioxido-4-thiomorpholinyl)-3,5-difluorophenylcarbamate (8.695 g, 24.02 mmol, prepared according to the procedures described in U.S. patent application Ser. No. 60/285,588) and DDQ (16.36 g, 72.06 mmol) in p-dioxane under an atmosphere of nitrogen is heated to reflux and stirred for a further 22 hrs to give a dark red/brown solution. The cooled reaction mixture is treated with 10% aqueous sodium sulfite solution (100 ml) and stirred for a further 1 hr. The solution is diluted with water (500 ml) and extracted with EtOAc (250 ml). The layers are separated and the aqueous layer is extracted with EtOAc (2×250 ml). The combined organic layers are washed with saturated aqueous NaHCO₃ solution (2×450 ml), dried (Na₂SO₄), filtered and concentrated under reduced pressure to give a brown oil. The oil is dissolved in dichloromethane (100 ml) and filtered through a coarse glass frit, then concentrated to a volume of ca. 40 ml. This solution is loaded onto silica gel (180 g) and eluted with 40:1 dichloromethane/diethyl ether (increase gradient to 10:1 dichloromethane/diethyl ether) to give the desired product (2.97 g, 35%). The impure fractions are recombined and subjected to repeated chromatography.

MS: m/z (ES+) 361 (100%, [M+H]⁺); (ES−) 359 (100%, [M−H]⁻). ¹H NMR: (400 MHz, CDCl₃, ppm) δ 7.18 (d, J=10.0 Hz, 2H), 6.55 (d, J=9.0 Hz, 1H), 5.40 (d, J=9.0 Hz, 1H), 4.11 (m, 2H), 3.97 (d, J=6.6 Hz, 2H), 3.33 (m, 2H), 1.98 (septet, J=6.7 Hz, 1H), 0.97 (d, J=6.8 Hz, 6H).

Step 2. Preparation of N-[[(5S)-3-[4-(2,3-dihydro-1,1-dioxido-4H-1,4-thiazin-4-yl)-3,5-difluorophenyl]-2-oxo-5-oxazolidinyl]methyl]acetamide.

A solution of the carbamate from the previous step (473 mg, 1.314 mmol) and N-[(2S)-2-(acetyloxy)-3-chloropropyl]acetamide (509 mg, 2.628 mmol, prepared according to the procedure described in Tetrahedron Letters, Vol. 37, No. 44, pp. 7937–7940 and WO 9924393) in acetonitrile (6 ml), THF (2 ml) and MeOH (0.11 ml) at 1–5° C. under an atmosphere of nitrogen was added lithium tert-butoxide portionwise (316 mg, 3.942 mmol; as 10 portions over 35 minutes). After each addition THF was added (5 ml), and after completion of addition the reaction was stirred for a further 40 minutes at 1–5° C. then warmed to room temperature and stirred for a further 26 hours. Water (15 ml) was added, then saturated aqueous ammonium chloride (15 ml), and then extracted with dichloromethane (4×30 ml). The combined organic extracts were dried (Na$_2$SO$_4$), filtered and concentrated under reduced pressure to give a pale brown solid. Trituration with chloroform and filtration afforded the product as a white solid (377 mg, 71%).

MS: m/z (ES+) 402 (12%, [M+H]$^+$), 107 (100%), 169 (92%). $^1$H NMR: (400 MHz, DMSO-d$_6$, ppm) δ 8.30 (t, J=5.7 Hz, 1H), 7.50 (d, J=10.6 Hz, 2H), 6.97 (d, J=8.9 Hz, 1H), 5.53 (d, J=8.9 Hz, 1H), 4.82 (m, 1H), 4.18 (t, J=9.1 Hz, 1H), 4.05 (m, 2H), 3.78 (dd, J=9.2 and 6.5 Hz, 1H), 3.47 (t, J=5.4 Hz, 2H), 3.39 (s, 3H and m, 2H), 1.89 (s, 3H)

Example 9

Preparation of N-[[(5S)-3-[4-(3,4-dihydro-1,1-dioxido-2H-thiopyran-4-yl)-3-fluorophenyl]-2-oxo-5-oxazolidinyl]methyl]-2,2-difluoroacetamide

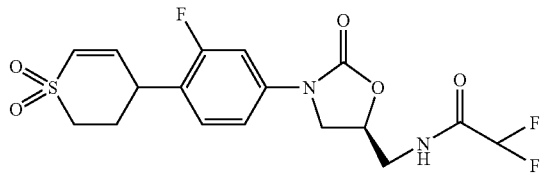

Step 1. Preparation of (5S)-5-(aminomethyl)-3-[4-(3,4-dihydro-1,1-dioxido-2H-thiopyran-4-yl)-3-fluorophenyl]-2-oxazolidinone monohydrochloride.

The product of Example 5 (1.34 g, 3.50 mmol) is suspended in a mixture of concentrated hydrochloric acid (20 ml) and methanol (75 ml) and heated at about 70° C. overnight. The reaction mixture is evaporated to dryness to provide the crude amine hydrochloride as a solid. MS (m/z): [M+H]$^+$=341.

Step 2. Preparation of N-[[(5S)-3-[4-(3,4-dihydro-1,1-dioxido-2H-thiopyran-4-yl)-3-fluorophenyl]-2-oxo-5-oxazolidinyl]methyl]-2,2-difluoroacetamide.

The above amine hydrochloride (1.00 g, 2.65 mmol), ethyl difluoroacetate (0.659 g, 5.31 mmol), and triethylamine (0.78 ml, 5.57 mmol) in methanol (20 ml) are stirred at room temperature overnight. The reaction mixture is evaporated to dryness and the residue purified by PTLC (10% MeOH/DCM) to give the title compund as solid. R$_f$ (10% MeOH/DCM)=0.53.

MS (m/z): [M+H]$^+$=419. $^1$H NMR (300 MHz, DMSO-d$_6$): 2.17–2.28 (m, 1H), 2.38–2.42 (m, 1 h), 3.22–3.48 (m, 2H), 3.53 (t, J=5.5 Hz, 2 H), 3.77 (dd, J=6.3 and 9.1 Hz, 1H), 4.00–4.03 (m, 1H), 4.14 (dt, J=1.1 and 9.3 Hz), 4.76–4.85 (m, 1H), 6.24 (t, J=54 Hz, 1H), 6.43–6.50 (m, 1H), 6.77 (m, 1H), 7.21 (t, J=8.5 Hz, 1H), 7.29 (dd, J=1.9 and 8.5 Hz, 1H), 7.52 (dd, J=2.2 and 11.5 Hz, 1H), 9.14 (t, J=5.8 Hz, 1H).

Example 10

Preparation of N-[[(5S)-3-[4-(3,4-dihydro-1,1-dioxido-2H-thiopyran-4-yl)-3-fluorophenyl]-2-oxo-5-oxazolidinyl]methyl]-2,2-difluoroethanethioamide

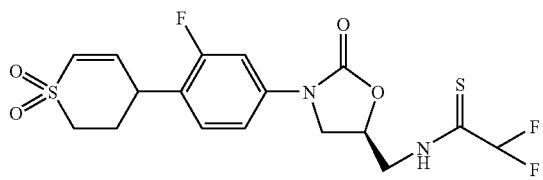

The product of Example 9 (0.40 g, 0.956 mmol) and Lawesson's reagent (0.290 g, 0.717 mmol) in dioxane (5 ml) are heated at 80° C. overnight. The reaction mixture is evaporated to dryness and the residue purified by PTLC (10% MeOH/DCM) to give the title compound as solid. R$_f$ (10% MeOH/DCM)=0.66.

MS (m/z): [M+H]$^+$=435. $^1$H NMR (300 MHz, DMSO-d$_6$): 2.17–2.29 (m, 1H), 2.38–2.42 (m, 1H), 3.23–3.48 (m, 2H), 3.83–3.92 (dd, J=6.0 and 8.8 Hz, 1H), overlapping 3.97 (t, J=8.2 Hz, 2 H) and 4.00–4.04 (m, 1H), 4.18 (dt, J=1.1 and 9.3 Hz, 1H), 4.98–5.07 (m, 1H), overlapping 6.43–6.50 (m, 1H) and 6.48 (t, J=55 Hz, 1H), 6.77 (m, 1H), 7.22 (t, J=8.5 Hz, 1H), 7.31 (dd, J=2.2 and 8.5 Hz, 1H), 7.53 (dd, J=2.2 and 12.9 Hz, 1H), 11.1 (br. t, 1H).

Example 11

Preparation of 2,2-dichloro-N-[[(5S)-3-[4-(3,4-dihydro-1,1-dioxido-2H-thiopyran-4-yl)-3-fluorophenyl]-2-oxo-5-oxazolidinyl]methyl]acetamide

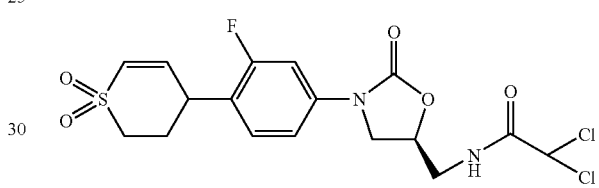

Dichloroacetic anhydride (0.13 ml, 0.831 mmol) is added to the amine hydrochloride prepared in Step 1 of Example 9 (0.241 g, 0.640 mmol) in pyridine (5 ml) at 0° C. and then stirred at room temperature for about 2 hours. The reaction mixture is evaporated to dryness and the residue is purified by PTLC (10% MeOH/DCM) to give the title compound as solid. R$_f$ (10% MeOH/DCM)=0.56; mp 148–50.

MS (m/z): [M+H]$^+$=452. $^1$H NMR (300 MHz, DMSO-d$_6$): 2.17–2.29 (m, 1H), 2.38–2.42 (m, 1H), 3.22–3.48 (m, 2H), 3.53 (t, J=5.5 Hz, 2H), 3.74 (dd, J=6.3 and 9.1 Hz, 1H), 3.99–4.04 (m, 1H), 4.14 (dt, J=1.1 and 9.3 Hz), 4.77–4.85 (m, 1H), overlapping 6.43–6.50 (m, 1H) and 6.48 (s, 1H), 6.78 (m, 1H), 7.21 (t, J=8.5 Hz, 1H), 7.28 (dd, J=2.2 and 8.5 Hz, 1H), 7.52 (dd, J=2.2 and 12.9 Hz, 1H), 8.97 (t, J=5.8 Hz, 1H).

Example 12

Preparation of N-[[(5S)-3-[4-(3,4-dihydro-4-hydroxy-1,1-dioxido-2H-thiopyran-4-yl)-3-fluorophenyl]-2-oxo-5-oxazolidinyl]methyl]acetamide

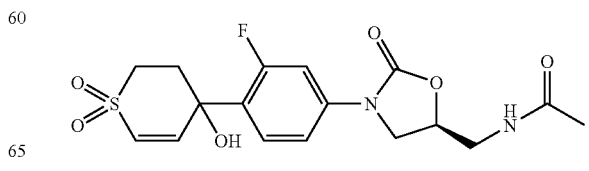

Step 1. Preparation of N-[[(5S)-3-[4-(3,4-dihydroxy-1,1-dioxido-2H-thiopyran-4-yl)-3-fluorophenyl]-2-oxo-5-oxazolidinyl]methyl]acetamide.

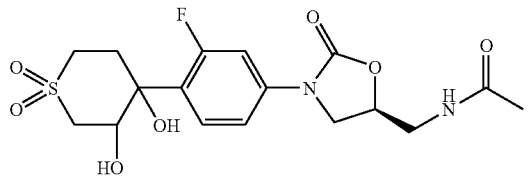

A solution of (S)-N-[[3-[4-(3,6-dihydro-1,1-dioxido-2H-thiopyran-4-yl)-3-fluorophenyl]-2-oxo-5-oxazolidinyl]methyl]acetamide (0.415 g, 1.08 mmol; prepared as described in U.S. Pat. No. 5,968,962) in 1:1 t-butanol-water (4 mL) is added to a solution of the standard reagent AD mix-β (1.51 g; available from Aldrich Co.) and methanesulfonamide (0.103 g, 1.08 mmol) in 1:1 t-butanol-water (10 mL) cooled at 0° C. The reaction mixture is stirred 5 days at 4° C. and then treated with sodium sulfite (1.5 g) and stirred 30 minutes. The solution is then extracted with four 10 mL portions of ethyl acetate and the combined organic phases dried (MgSO$_4$), filtered and concentrated. Purification by column chromatography (0–5% MeOH-DCM) provided the title compound as a mixture of diastereomers. Yield 0.29 g (64%). $^1$H NMR.

Step 2. Preparation of N-[[(5S)-3-[4-(3,4-dihydro-4-hydroxy-1,1-dioxido-2H-thiopyran-4-yl)-3-fluorophenyl]-2-oxo-5-oxazolidinyl]methyl]acetamide.

Methanesulfonyl chloride (0.019 mL, 0.25 mmol) is added to a solution of the product of Step 1 (0.026 g, 0.063 mmol) in 2:1 dichloromethane-triethylamine (3 mL). After 30 minutes, additional methanesulfonyl chloride (0.008 mL, 0.13 mmol) is added and the mixture allowed to warm to room temperature. After another 30 minutes, 1.0 mL of 2.5% NaHCO$_3$ is added and the mixture concentrated. The resulting aqueous solution is extracted with three 10 mL portions of ethyl acetate and the combined organic phases dried (MgSO$_4$), filtered and concentrated to provide the crude methanesulfonic acid ester. This material is dissolved in acetonitrile (1 mL) and DBU (0.034 mL, 0.23 mmol) and heated to 55° C. for 1.5 hours. The solution is then concentrated and purified by preparative TLC (5% MeOH-DCM) to provide the title compound as a mixture of diastereomers.

MS (m/z): [M+H]$^+$=399; $^1$H NMR (300 MHz, CDCl$_3$): 1.93 (s, 3H), 2.27–2.33 (m, 1H), 2.80–3.11 (m, 2H), 3.44–3.75 (m, 5H), 3.98–4.05 (d tr, J=9, 2 Hz, 1H), 4.68–4.76 (m, 1H), 6.28 (d, J=11 Hz, 1H), 6.35 (dd, J=11, 2 Hz, 1H), 7.15 (d, J=8 Hz, 1H), 7.39 (dd, J=14, 2 Hz, 1H), 7.55 (tr, J=9 Hz, 1H), 7.74 (tr, J=6 Hz, 1H).

Example 13

Preparation of N-[[(5S)-3-[3-fluoro-4-(4-fluoro-3,4-dihydro-1,1-dioxido-2H-thiopyran-4-yl)phenyl]-2-oxo-5-oxazolidinyl]methyl]acetamide

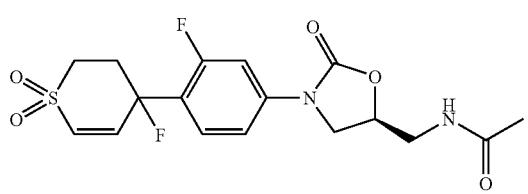

(N,N-Dimethylamino)sulfur trifluoride (2.5 μL, 0.019 mmol) is added to a cooled (−78° C.) solution of the product of Example 12 (6.0 mg, 0.014 mmol) in DCM (0.75 mL).

The solution is warmed slowly to room temperature over 4 hours and diluted with ethyl acetate. The organic solution is extracted with satd NaHCO$_3$, H$_2$O, brine and dried (Na$_2$SO$_4$). The crude product is purified by preparative TLC (7% MeOH-DCM) to provide the title compound as a mixture of diastereomers.

MS (m/z): [M+H]$^+$=401; $^1$H NMR (300 MHz, CDCl$_3$): 2.03 (s, 3H), 2.64–2.73 (m, 1H), 2.98–3.24 (m, 2H), 3.56–3.83 (m, 4H), 4.03–4.10 (m, 1H), 4.77–4.85 (m, 1H), 5.95 (tr, J=6 Hz, 1H), 6.36 (d, J=11 Hz, 1H), 6.61 (dtr, J=11, 3 Hz, 1H), 7.25 (d, J=9 Hz, 1H), 7.47 (tr, J=9 Hz, 1H), 7.55 (d tr, J=13, 2 Hz, 1H).

Example 14

Preparation of N-[[(5S)-3-[4-(3,4-dihydro-1,1-dioxido-2H-thiopyran-4-yl)phenyl]-2-oxo-5-oxazolidinyl]methyl]acetamide

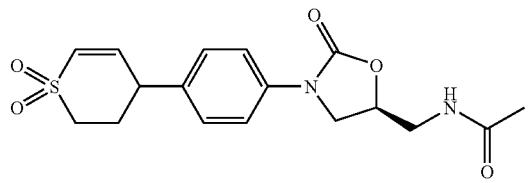

Trifluoroacetic anhydride (2.98 mL, 21.1 mmol) is added dropwise at room temperature to a solution of N-[[(5S)-3-[4-(tetrahydro-1-oxido-2H-thiopyran-4-yl)phenyl]-2-oxo-5-oxazolidinyl]methyl]acetamide (2.46 g, 7.02 mmol; prepared as described in International Publication WO 97/09328) and N-methylmorpholine (3.86 mL, 35.1 mmol) in dichloromethane (60 mL). The reaction mixture is stirred overnight at room temperature and then evaporated to dryness. The resulting crude N-[[(5S)-3-[4-(3,4-dihydro-2H-thiopyran-4-yl)phenyl]-2-oxo-5-oxazolidinyl]methyl]acetamide (2.77 g) is dissolved in tetrahydrofuran (100 mL) and peracetic acid (7.01 mL of a 32% solution in acetic acid) added dropwise at 0° C. The reaction mixture is allowed to warm to room temperature, stirred overnight, and then evaporated to dryness. The residue is purified by flash column chromatography (ethyl acetate) to give the title compound as white solid.

M.p. 187–9° C. MS (m/z): [M+H]$^+$=365. $^1$H NMR (300 MHz, DMSO-d$_6$): 1.82 (s, 3H), 2.10–2.23 (m, 1H), 2.39–2.48 (m, 1H), 3.21–3.31 (m, 2H), 3.40 (t, J=5.5 Hz, 2H), 3.69–3.75 (m, 1H), 3.77–3.84 (m, 1H), 4.10 (dt, J=1.9 and 8.9 Hz, 1H), 4.66–4.74 (m, 1H), 6.47 (m, 1H), 6.76 (m, 1H), 7.22 (d, J=8.5 Hz, 2H), 7.53 (d, J=8.5 Hz, 2H), 8.24 (br. t, J=5.8 Hz, 1H).

Example 15

Preparation of N-[[(5S)-3-[4-(3,4-dihydro-1,1-dioxido-2H-thiopyran-4-yl)phenyl]-2-oxo-5-oxazolidinyl]methyl]-2,2-difluoroacetamide

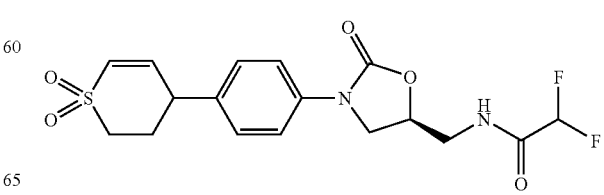

Step 1. Preparation of (5S)-5-(aminomethyl)-3-[4-(3,4-dihydro-1,1-dioxido-2H-thiopyran-4-yl)phenyl]-2-oxazolidinone monohydrochloride.

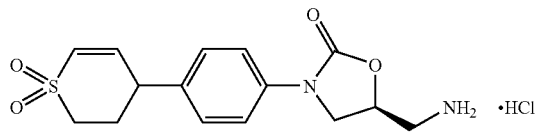

N-[[(5S)-3-[4-(3,4-Dihydro-1,1-dioxido-2H-thiopyran-4-yl)phenyl]-2-oxo-5-oxazolidinyl]methyl]acetamide, prepared as described in Example 14 (1.90 g, 5.21 mmol) is suspended in a mixture of concentrated hydrochloric acid (25 mL) and methanol (75 mL), and heated at 70° C. overnight. The reaction mixture is evaporated to dryness to give the title compound as white solid, which is used directly in the next step. MS (m/z): [M+H]⁺=323.

Step 2. Preparation of N-[[(5S)-3-[4-(3,4-dihydro-1,1-dioxido-2H-thiopyran-4-yl)phenyl]-2-oxo-5-oxazolidinyl]methyl]-2,2-difluoroacetamide.

The crude amine hydrochloride salt from Step 1 (0.350 g, 0.975 mmol), ethyl difluoroacetate (0.605 g, 4.88 mmol), and triethylamine (0.27 ml, 1.95 mmol) in methanol (5 mL) are stirred at r.t. overnight. The reaction mixture is evaporated to dryness and the residue purified by PTLC (10% methanol/dichloromethane) to give the title compound as white solid (0.30 g, 78%). M.p. 135–6° C.

MS (m/z): [M+H]⁺=401. ¹H NMR (300 MHz, DMSO-d₆): 2.10–2.23 (m, 1H), 2.39–2.49 (m, 1H), 3.21–3.41 (m, 2H), 3.52 (t, J=5.8 Hz, 2H), 3.74–3.83 (m, 2H), 4.14 (dt, J=1.9 and 9.1 Hz, 1H), 4.74–4.83 (m, 1H), 6.25 (t, J=53.6 Hz, 1H), 6.47 (m, 1H), 6.76 (m, 1H), 7.22 (d, J=8.5 Hz, 2H), 7.52 (d, J=8.52 Hz, 2H), 9.17 (br. t, J=5.8 Hz, 1H).

Example 16

Preparation of 2,2-dichloro-N-[[(5S)-3-[4-(3,4-dihydro-1,1-dioxido-2H-thiopyran-4-yl)phenyl]-2-oxo-5-oxazolidinyl]methyl]acetamide

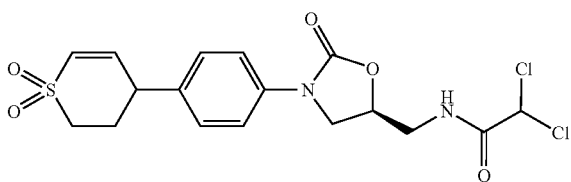

The crude amine hydrochloride prepared in Step 1 of Example 15 (0.350 g, 0.975 mmol), ethyl dichloroacetate (0.60 ml, 4.88 mmol), and triethylamine (0.27 ml, 1.95 mmol) in methanol (5 mL) are stirred at r.t. overnight. The reaction mixture is evaporated to dryness and the residue purified by PTLC (10% methanol/dichloromethane) to give the title compound as white solid (0.32 g, 75%). M.p. 159–61° C.

MS (m/z): [M+H]⁺=434. ¹H NMR (300 MHz, DMSO-d₆): 2.09–2.22 (m, 1H), 2.39–2.49 (m, 1H), 3.21–3.40 (m, 2H), 3.53 (t, J=5.8 Hz, 2H), 3.70–3.76 (m, 1H), 3.78–3.83 (m, 1H), 4.13 (dt, J=2.2 and 9.1 Hz, 1H), 4.75–4.83 (m, 1H), overlapping 6.42–6.50 (m, 1H) and 6.48 (s, 1H), 6.75 (m, 1H), 7.22 (d, J=8.8 Hz, 2H), 7.52 (d, J=8.8 Hz, 2H), 8.98 (br. t, J=5.8 Hz, 1H).

Example 17

Preparation of [[(5S)-3-[4-(3,4-dihydro-1,1-dioxido-2H-thiopyran-4-yl)phenyl]-2-oxo-5-oxazolidinyl]methyl]-2,2-difluoroethanethioamide

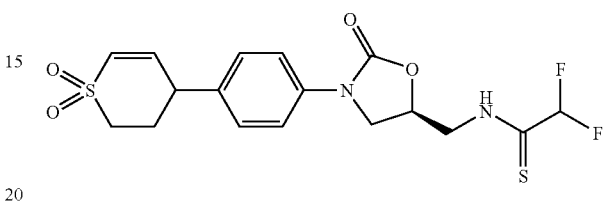

Step 1. Preparation of difluoroacetic acid, O-(3,3-diphenyl-propyl)ester.

Dicyclohexylcarbodiimide (12.6 g, 62.4 mmol) is added portionwise with stirring to a solution of difluoroacetic acid (4.0 g, 4.0 mL, 62.4 mmol), 3,3-diphenyl-1-propanol (14.4 g, 13.8 mL, 68.4 mol) and 4-dimethylaminopyridine (732 mg, 6.2 mmol) in ethyl ether (180 mL) at 0–5° C. The reaction mixture is allowed to warm up to r.t., and stirred at r.t. overnight. The precipitated urea by-product is filtered off and washed with excess ethyl ether. The combined filtrates are evaporated under vacuum, and the residue is purified by silica gel flash chromatography (eluent: 5% ethyl ether in hexanes). White crystalline solid (17.3 g, 96%). HPLC R$_t$=7.2. MS (m/z): 291 [M+H]⁺.

Step 2. Preparation of difluorothioacetic acid, O-(3,3-diphenyl-propyl)ester.

A solution of the ester prepared in the previous step (17.3 g, 59.7 mmol) in xylene (100 mL) is treated with Lawesson's reagent (29.0 g, 71.6 mmol), and the reaction mixture is stirred at 135–145° C. for 24 h. The resulting solids are filtered off and washed with an excess of ethyl acetate. The combined filtrates are evaporated under vacuum, and the residue is purified by silica gel flash chromatography (eluent: hexanes). Yellow oil (9.6 g, 53%). HPLC R$_t$=7.6. MS (m/z): 307 [M+H]⁺.

Step 3. Preparation of [[(5S)-3-[4-(3,4-dihydro-1,1-dioxido-2H-thiopyran-4-yl)phenyl]-2-oxo-5-oxazolidinyl]methyl]-2,2-difluoroethanethioamide.

The crude amine hydrochloride prepared in Step 1 of Example 15 (0.350 g, 0.975 mmol), the product of step 2 immediately above (0.358 g, 1.17 mmol), and triethylamine (0.27 ml, 1.95 mmol) in methanol are stirred at room temperature overnight. The reaction mixture is evaporated to dryness and the residue purified by PTLC (10% methanol/dichloromethane) to give the title compound as white solid (0.29 g, 70%). M.p. 139–40° C.

MS (m/z): [M+H]⁺=417. ¹H NMR (300 MHz, DMSO-d₆): 2.10–2.23 (m, 1H), 2.39–2.49 (m, 1H), 3.20–3.41 (m, 2H), 3.78–3.90 (m, 2H), 3.97 (t, J=5.2 Hz, 2H), 4.18 (dt, J=2.2 and 8.8 Hz, 1H), 4.96–5.05 (m, 1H), overlapping 6.45–6.50 (m, 1H) and 6.49 (tr, J=64 Hz, 1H), 6.76 (m, 1H), 7.23 (d, J=8.8 Hz, 2H), 7.53 (d, J=8.8 Hz, 2H), 11.10 (br. t, J=4.5 Hz, 1H).

Example 18

Preparation of N-[[(5S)-3-[4-(3,4-dihydro-1,1-dioxido-2H-thiopyran-4-yl)phenyl]-2-oxo-5-oxazolidinyl]methyl]propionamide

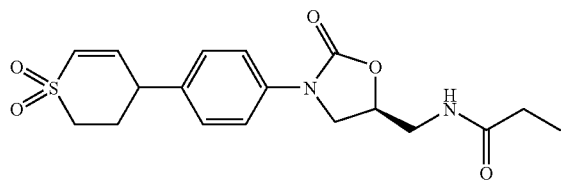

Propionic anhydride (0.136 ml, 1.06 mmol) is added dropwise to the crude amine hydrochloride prepared in Step 1 of Example 15 (0.316 g, 0.88 mmol) in a mixture of pyridine (4 mL) and dichloromethane (4 mL). The mixture is stirred for 4 hours and then evaporated to dryness. The residue is purified by PTLC (10% methanol/dichloromethane) to give the title compound as white solid (0.28 g, 80%). M.p. 144–7° C.

MS (m/z): $[M+H]^+=401$. $^1H$ NMR (300 MHz, DMSO-$d_6$): 0.94 (t, J=7.7 Hz, 3H), overlapping 2.08 (q, J=7.7 Hz, 2H) and 2.14–2.23 (m, 1H), 2.39–2.47 (m, 1H), 3.21–3.43 (m, 4H), 3.70–3.76 (m, 1H), 3.77–3.84 (m, 1H), 4.10 (dt, J=2.2 and 8.8 Hz, 1H), 4.67–4.75 (m, 1H), 6.47 (m, 1H), 6.75 (m, 1H), 7.22 (d, J=8.8 Hz, 2H), 7.52 (d, J=8.5 Hz, 2H), 8.16 (br. t, J=6.0 Hz, 1H).

Example 19

Preparation of (S)-[[3-[4-(3,4-dihydro-1,1-dioxido-2H-thiopyran-4-yl)phenyl]-2-oxo-5-oxazolidinyl]methyl]carbamic acid, methyl ester

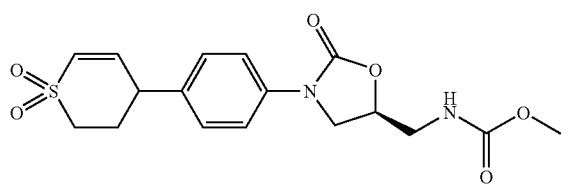

Methyl chloroformate (0.072 mL, 0.925 mmol) is added dropwise at 0° C. to to the crude amine hydrochloride prepared in Step 1 of Example 15 (0.316 g, 0.881 mmol) in a mixture of pyridine (4 mL) and dichloromethane (4 mL). The mixture is allowed to warm to room temperature, stirred for 1 hour, and then evaporated to dryness. The residue is purified by PTLC (10% methanol/dichloromethane) to give white solid (0.26 g, 78%). M.p. 196–7° C.

MS (m/z): $[M+H]^+=379$. $^1H$ NMR (300 MHz, DMSO-$d_6$): 2.10–2.23 (m, 1H), 2.39–2.47 (m, 1H), 3.21–3.40 (m, 4H), 3.52 (s, 3H), 3.73–3.84 (m, 2H), 4.10 (dt, J=2.2, and 8.8 Hz, 1H), 4.65–4.74 (m, 1H), 6.47 (m, 1H), 6.75 (m, 1H), 7.22 (d, J=8.5 Hz, 2H), 7.53 (d, J=8.8 Hz, 2H), 11.1 (br. t, J=4.7 Hz, 1H).

Example 20

Preparation of N-[[(5S)-3-[4-(3,4-dihydro-1,1-dioxido-2H-thiopyran-4-yl)-3,5-difluorophenyl]-2-oxo-5-oxazolidinyl]methyl]acetamide

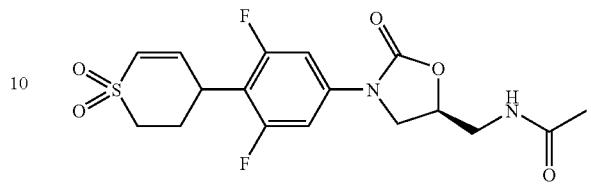

Step 1. Preparation of (3,5-difluorophenyl)carbamic acid, 1-methylethyl ester

Sodium bis(trimethylsilyl)amide (2.0M solution in tetrahydrofuran, 194 ml, 0.388 mol) was added dropwise to 3,5-difluoroaniline (25.0 g, 0.194 mol) in THF (100 mL) at 0° C. Isopropyl chloroformate (1 M solution in toluene, 291 mL, 0.291 mol) was then added dropwise at 0° C. and the mixture allowed to warm to room temperature over 1 h. The reaction mixture was quenched with 2N hydrochloric acid and extracted with ethyl acetate. The extract was washed with saturated aqueous sodium bicarbonate, brine, dried (MgSO$_4$), and then evaporated. The residue was triturated with hexane to give the title compound as solid.

$^1H$ NMR (300 MHz, CDCl$_3$): 1.27 (d, J=6.3 Hz, 6H), 4.99 (q, J=6.3 Hz, 1H), 6.42–6.50 (m, 1H), 6.65 (br. s, 1H), 6.92–6.97 (m, 2H).

Step 2. Preparation of [3,5-difluoro-4-(tetrahydro-4-hydroxy-2H-thiopyran-4-yl)phenyl]carbamic acid, 1-methylethyl ester.

n-Butyllithium (2.5M in hexanes, 57.2 mL, 0.143 mol) was added dropwise with stirring at –78° C. to (3,5-difluorophenyl)-carbamic acid isopropyl ester (15.0 g, 0.07 mol) and N,N,N',N'-tetramethylethylenediamine (21.04 mL, 0.139 mol) in THF (150 mL), and stirred for 20 min at this temperature. Tetrahydrothiopyran-4-one (8.50 g, 0.073 mol) dissolved in THF (10 mL) was then added dropwise at –78° C., stirred for 1 h, and then allowed to warm to room temperature. The reaction was stirred for another hour and then quenched with saturated aqueous ammonium chloride (100 mL). The reaction mixture was extracted with ethyl acetate, the extracts washed with brine, dried (MgSO$_4$), and evaporated. The residue was purified by flash column chromatography (30% ethyl acetate/hexane) to give the title compound as white solid.

MS (m/z): $[M+H]^+=332$. $^1H$ NMR (300 MHz, DMSO-$d_6$): 1.24 (d, J=6.3 Hz, 6H), 2.14 (m, 4H), 2.28–2.33 (m, 2H), 2.93–3.15 (m, 2H), 4.83–4.92 (m, 1H), 5.18 (s, 1H), 7.05 (d, J=13.2 Hz, 2H), 9.90 (s, 1H).

Step 3. Preparation of N-[[(5S)-3-[3,5-difluoro-4-(tetrahydro-1-oxido-2H-thiopyran-4-yl)phenyl]-2-oxo-5-oxazolidinyl]methyl]acetamide.

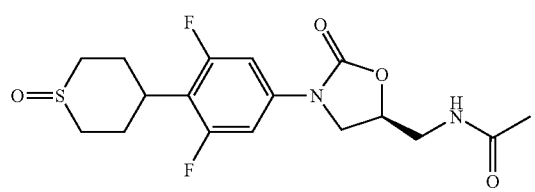

[3,5-Difluoro-4-(tetrahydro-4-hydroxy-2H-thiopyran-4-yl)phenyl]carbamic acid, 1-methylethyl ester (from Step 2) is converted to the product following the method described in the International Publication WO 00/44741.

Step 4. Preparation of N-[[(5S)-3-[4-(3,4-dihydro-1,1-dioxido-2H-thiopyran-4-yl)-3,5-difluorophenyl]-2-oxo-5-oxazolidinyl]methyl]acetamide.

Trifluoroacetic anhydride (2.24 ml, 15.8 mmol) was added dropwise at room temperature to a solution of N-[[(5S)-3-[3,5-difluoro-4-(tetrahydro-1-oxido-2H-thiopyran-4-yl)phenyl]-2-oxo-5-oxazolidinyl]methyl]acetamide (2.04 g, 5.28 mmol and N-methylmorpholine (2.90 ml, 26.4 mmol) in dichloromethane (50 ml). The reaction mixture was stirred overnight at room temperature and then evaporated to dryness. The resulting crude N-({(5S)-3-[4-(3,4-dihydro-2H-thiopyran-4-yl)-3,5-difluorophenyl]-2-oxo-1,3-oxazolidin-5-yl}methyl)acetamide (1.95 g) was dissolved in tetrahydrofuran (100 ml) and peracetic acid (5.6 ml of a 32% solution in acetic acid, 26.4 mmol) added dropwise at 0° C. The reaction mixture was allowed to warm to room temperature, stirred overnight, and then evaporated to dryness. The residue was purified by flash column chromatography (ethyl acetate) to give white solid (1.80 g, 85%).

MS (m/z): [M+H]$^+$=401. $^1$H NMR (300 Mhz, DMSO): 1.82 (s, 3H), 2.26–2.45 (m, 2H), overlapping 3.35–3.41 (m, 1H) and 3.40 (t, J=5.5 hz, 1H), 3.49–3.59 (m, 1H), 3.71 (dd, J=6.6, 9.1 hz, 1H), 4.07–4.13 (m, 2H), 4.70–4.78 (m, 1H), 6.47 (m, 1H); 6.70 (d tr, J=2.5, 10.9 hz, 1H); 7.31 (s, 1H); 7.34 (s, 1H); 8.24 (t, J=5.8 hz, 1H).

Example 21

Preparation of N-[[(5S)-3-[4-(2,3-dihydro-1,1-dioxido-4H-1,4-thiazin-4-yl)-3-fluorophenyl]-2-oxo-5-oxazolidinyl]methyl]-2,2-difluoroethanethioamide

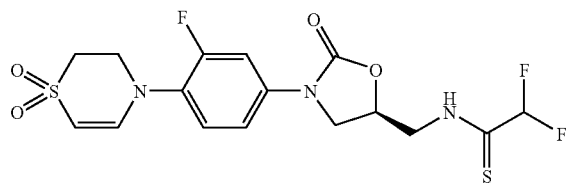

Step 1. Preparation of [[(5S)-3-[3-fluoro-4-(tetrahydro-4H-1,4-thiazin-4-yl)phenyl]-2-oxo-5-oxazolidinyl]methyl]carbamic acid, 1,1-dimethylethyl ester.

A solution of [3-fluoro-4-(4-thiomorpholinyl)phenyl]carbamic acid, phenylmethyl ester (Barbachyn, et al, *J. Med. Chem.* 1996, 39, 680–5.) (8.7 g, 25 mmol) in DMF (17 mL) is cooled at 0° C. and treated with (3-chloro-2-hydroxypropyl)-carbamic acid tert-butyl ester (6.6 g, 31 mmol, prepared according to the procedure described in U.S. patent application Ser. No. 09/982,157) and then lithium tert-butoxide (60 mL of a 1.0 M solution in THF) dropwise over 15 min. The reaction mixture is stirred for 20 h at room temperature and then treated with 50 mL of satd. NH$_4$Cl and 100 mL of H$_2$O. The solution is extracted with two portions of dichloromethane and the combined organic phases washed with H$_2$O, brine and dried (MgSO$_4$), filtered and concentrated. The crude product is purified by column chromatography (0–50% ethyl acetate-hexanes) to provide the title compound as a solid.

Step 2. Preparation of [[(5S)-3-[3-fluoro-4-(tetrahydro-1-oxido-4H-1,4-thiazin-4-yl)phenyl]-2-oxo-5-oxazolidinyl]methyl]carbamic acid, 1,1-dimethylethyl ester.

Sodium periodate (3.5 g, 16.5 mmol) is added to a suspension of the product from Step 1 (6.5 g, 15.7 mmol) in 250 mL of 2:1 methanol:H$_2$O. The mixture is stirred for 3 days at 4° C. in a cold room and then filtered to remove solids. The solids are washed with CHCl$_3$ and the combined filtrate concentrated to give an aqueous solution that is diluted with H$_2$O. This aqueous solution is extracted with five portions of CHCl$_3$ and the combined organic extracts are dried (Na$_2$SO$_4$), filtered and concentrated to provide the title compound, which is used without further purification.

Step 3. Preparation of [[(5S)-3-[4-[2,3-dihydro-6-(trifluoroacetyl)-4H-1,4-thiazin-4-yl]-3-fluorophenyl]-2-oxo-5-oxazolidinyl]methyl]carbamic acid, 1,1-dimethylethyl ester.

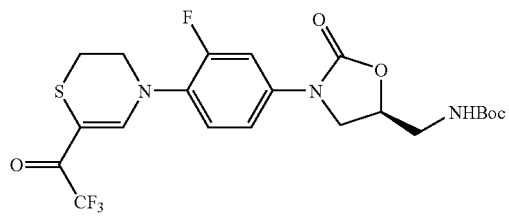

4-Methylmorpholine (2.14 mL, 1.97 g, 19.5 mmol) is added to a solution of the product from Step 2 (1.39 g, 3.25 mmol)) in DCM (60 mL) at 0° C., followed by trifluoroacetic anhydride (1.8 mL, 2.7 g, 13 mmol). The solution is stirred at r.t. for 20 h, concentrated under vacuum, and then dissolved in 100 mL of EtOAc—2.5% aq. NaHCO$_3$ (1:1). The layers are separated and the aqueous phase is extracted with EtOAc (2×50 mL). The combined organic layers are washed with brine and dried (MgSO$_4$). Solvent is removed under vacuum to afford the crude title compound as a foam that is used directly without further purification.

Step 4. Preparation of [[(5S)-3-[4-[2,3-dihydro-1,1-dioxido-6-(trifluoroacetyl)-4H -1,4-thiazin-4-yl]-3-fluorophenyl]-2-oxo-5-oxazolidinyl]methyl]carbamic acid, 1,1-dimethylethyl ester.

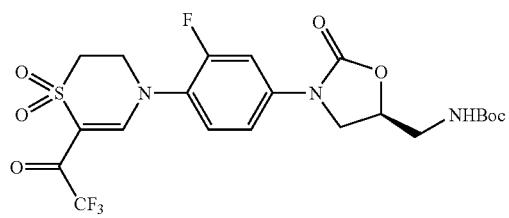

m-Chloroperoxybenzoic acid (2.3 g of a 60% Aldrich material, 8.1 mmol) is added to a cooled (0° C.) solution of the product from Step 3 (3.25 mmol) in DCM (60 mL), and the mixture is stirred at r.t. for 3 h. The reaction mixture is then quenched by the addition of 3 mL of satd. Na$_2$S$_2$O$_3$. The mixture is poured into dilute NaHCO$_3$ and extracted three times with dichloromethane. The combined organic extracts are washed with satd. NaHCO$_3$, brine and dried (MgSO$_4$), filtered and concentrated to provide the title compound as foam, which is used in the next step without further purification.

Step 5. Preparation of [[(5S)-3-[4-(2,3-dihydro-1,1-dioxido-4H-1,4-thiazin-4-yl -3-fluorophenyl]-2-oxo-5-oxazolidinyl]methyl]carbamic acid, 1,1-dimethylethyl ester.

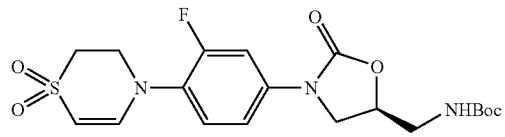

The crude product of Step 4 (3.25 mmol) is suspended in 60 mL of MeOH-acetonitrile (2:1) and heated to reflux. Solid $K_2CO_3$ (1.2 g, 8.7 mmol) is then added, and the mixture stirred at reflux for 2 h. Upon cooling, the solution is filtered and the filtrate concentrated. The residue is dissolved in 50 mL of EtOAc—2.5% aq. $NaHCO_3$ (1:1), the layers separated, and the aqueous phase extracted with more ethyl acetate. The combined organic layers are washed with brine and dried ($MgSO_4$), filtered and concentrated. The resulting crude product is purified by column chromatography (0–3% MeOH—$CH_2Cl_2$) provided the title compound as a foam.

Step 6. Preparation of N-[[(5S)-3-[4-(2,3-dihydro-1,1-dioxido-4H-1,4-thiazin-4-yl)-3-fluorophenyl]-2-oxo-5-oxazolidinyl]methyl]-2,2-difluoroethanethioamide.

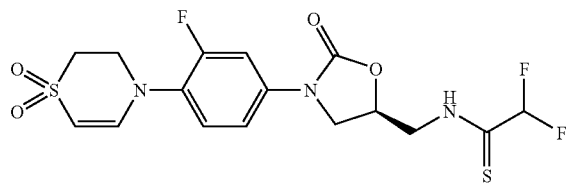

Trimethylsilyl trifluoromethanesulfonate (0.17 mL, 0.95 mmol) is added slowly over 15 min to a solution of the product from Step 5 (0.21 g, 0.47 mmol) and 2,6-lutidine (0.17 mL, 1.4 mmol) in dichloromethane (1 mL). The solution is stirred at room temperature for 1 h and then treated with methanol (1 mL). After 30 min, the solution is concentrated and redissolved in methanol (4 mL) and diisopropyl-ethylamine (0.25 mL, 1.4 mmol). A solution of difluoro-thioacetic acid O-(3,3-diphenyl-propyl) ester (the product of Example 17, step 2)(0.18 g, 0.59 mmol) in dichloromethane (0.75 mL) is then added and the solution stirred for 20 h at room temperature. The reaction mixture is then concentrated and the residue purified by column chromatography (0–1% MeOH-DCM) to provide the title compound.

MS (m/z): [M+H]+=436. $^1$H NMR (300 MHz, $CD_3OD$): 3.30–3.37 (m, 2H), 3.88–3.93 (m, 1H), 4.05–4.87 (m, 5H), 5.05–5.10 (m, 1H), 5.38 (d, J=9 Hz, 1H), 6.28 (t, J=54 Hz, 1H), 6.94 (d, J=9 Hz, 1H), 7.29–7.38 (m, 2H), 7.65 (dd, J=2 and 14 Hz, 1H).

Example 22

Preparation of 2,2-dichloro-N-[[(5S)-3-[4-(2,3-dihydro-1,1-dioxido-4H-1,4-thiazin-4-yl)-3-fluorophenyl]-2-oxo-5-oxazolidinyl]methyl]acetamide

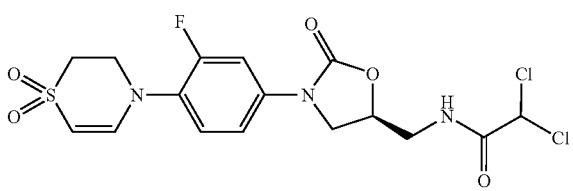

Following the procedures in Step 6 of Example 21, but using dichloroacetic anhydride (0.90 mmol) in pyridine (1 mL) as an acylating reagent and purification by column chromatography (0–1% MeOH-DCM), gives the title compound.

MS (m/z): [M+H]+=452. $^1$H NMR (300 MHz, $CD_3OD$): 3.30–3.37 (m, 2H), 3.64–3.67 (m, 2H), 3.81–3.87 (m, 1H), 4.14–4.20 (m, 3H), 4.87 (m, 1H), 5.38 (d, J=9 Hz, 1H), 6.25 (s, 1H), 6.93 (d, J=9 Hz, 1H), 7.31–7.37 (m, 2H), 7.64 (dd, J=3 and 14 Hz, 1H).

Example 23

Preparation of N-[[(5S)-3-[4-(2,3-dihydro-1,1-dioxido-4H-1,4-thiazin-4-yl)-3-fluorophenyl]-2-oxo-5-oxazolidinyl]methyl]-2,2-difluoroacetamide

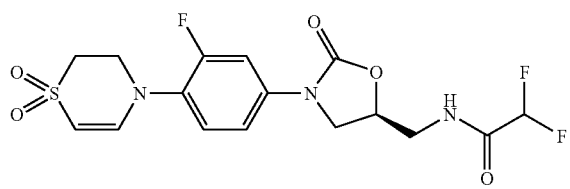

Following the procedures in Step 6 of Example 21, but using with ethyl difluoroacetate (0.85 mmol) in methanol (3.5 mL) and triethylamine (0.68 mmol) as an acylating reagent and purification by TLC (5% MeOH-DCM), gives the title compound.

MS (m/z): [M+H]+=420. $^1$NMR (300 MHz, $CD_3OD$): 3.32–3.38 (m, 2H), 3.62–3.84 (m, 3H), 4.13 (t, J=9 Hz, 1H), 4.19–423 (m, 2H), 4.84–4.88 (m, 1H), 5.41 (d, J=9 Hz, 1H), 5.95 (t, J=54 Hz, 1H), 6.77 (d, J=9 Hz, 1H), 7.21–7.25 (m, 2H), 7.59 (dd, J=1 and 12 Hz, 1H).

Example 24

Preparation of N-[[(5S)-3-[4-(2,3-dihydro-1,1-dioxido-4H-1,4-thiazin-4-yl)phenyl]-2-oxo-5-oxazolidinyl]methyl]-2,2-difluoroethanethioamide

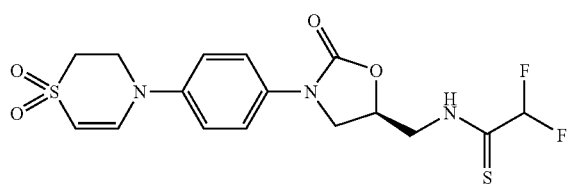

Step 1. Preparation of 4-(4-nitrophenyl)thiomorpholine.

Thiomorpholine (6.0 mL, 6.2 g, 60 mmol) is added to a solution of 1-fluoro-4-nitro-benzene (7.1 g, 50 mmol) and diisopropylethylamine (13 mL, 9.6 g, 75 mmol) in acetonitrile (90 mL). The solution is heated at reflux for 2 days, concentrated, and dissolved in ethyl acetate. The solution is washed with 100 mL each of 1 M HCl, sat. aq. $NaHCO_3$, and brine. The solution is dried ($MgSO_4$), filtered and concentrated to provide the title compound as solid.

Step 2. Preparation of [4-(4-thiomorpholinyl)phenyl]carbamic acid, phenylmethyl ester.

Iron powder (5.7 g, 101 mmol) is added in five portions over 1 h to a refluxing solution of 4-(4-nitrophenyl)thiomorpholine (7.6 g, 34 mmol) and ammonium chloride (18.0 g, 340 mmol) in 120 mL of 2:1 ethanol-$H_2O$. The rust colored mixture is refluxed for another 30 min and then cooled and filtered to remove iron oxide. 50 mL of $H_2O$ is added to the filtrate and the mixture concentrated to remove ethanol. The resulting aqueous solution is extracted with three portions of ethyl acetate and the combined organic phases washed with $H_2O$, brine, and dried ($MgSO_4$). Filtration and concentration gave the crude amine (6.1 g), which is dissolved in 104 mL of dichloromethane. Pyridine (5.1 mL, 4.9 g, 62 mmol) is added to the amine solution and after cooling to 0° C., benzyl chloroformate (5.1 mL, 6.1 g, 36 mmol) is added. The mixture is stirred for 20 h at 0° C. The reaction mixture is then diluted with dichloromethane and washed with $H_2O$, brine and then dried ($MgSO_4$). Concentration gave a solid that is triturated with hexane to afford the purified title compound solid.

Step 3. Preparation of [[(5S)-3-[4-(tetrahydro-4H-1,4-thiazin-4-yl)phenyl]-2-oxo-5-oxazolidinyl]methyl]carbamic Acid, 1,1-dimethylethyl ester.

A solution of the product of Step 2 (7.0 g, 21.3 mmol) in DMF (14 mL) is cooled at 0° C. and treated with (3-chloro-2-hydroxy-propyl)carbamic acid tert-butyl ester (5.6 g, 27 mmol) and then lithium tert-butoxide (51 mL of a 1.0 M solution in THF) dropwise over 15 min. The reaction mixture is stirred for 20 h at room temperature and then treated with 40 mL of satd. $NH_4Cl$ and 100 mL of $H_2O$. The solution is extracted with two portions of dichloromethane and the combined organic phases washed with $H_2O$, brine and dried ($MgSO_4$), filtered and concentrated. The crude product is purified by column chromatography (0–50% ethyl acetate-hexanes) to provide the title compound as a foam.

Step 4. Preparation of [[(5S)-3-[4-(tetrahydro-1-oxido-4H-1,4-thiazin-4-yl)phenyl]-2-oxo-5-oxazolidinyl]methyl]carbamic acid, 1,1-dimethylethyl ester.

Sodium periodate (1.7 g, 8.0 mmol) is added to a suspension of the product from Step 3 (3.0 g, 7.6 mmol) in 125 mL of 2:1 methanol:$H_2O$. The mixture is stirred for 20 h at 4° C. in a cold room and then filtered to remove solids. The solids are washed with $CHCl_3$ and the combined filtrate concentrated to give an aqueous solution that is diluted with $H_2O$. This aqueous solution is extracted with five portions of $CHCl_3$ and the combined organic extracts are dried ($Na_2SO_4$), filtered and concentrated to provide the crude product. Column chromatography (0–5% MeOH-DCM) provides the title compound as a foam.

Step 5. Preparation of [[(5S)-3-[4-[2,3-dihydro-6-(trifluoroacetyl)-4H-1,4-thiazin-4-yl]phenyl]-2-oxo-5-oxazolidinyl]methyl]carbamic acid, 1,1-dimethylethyl ester.

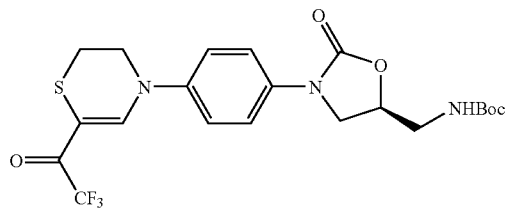

4-Methylmorpholine (4.4 mL, 4.1 g, 40 mmol) is added to a solution of the product from Step 4 (2.7 g, 6.7 mmol) in DCM (140 mL) at 0° C., followed by trifluoroacetic anhydride (3.8 mL, 5.6 g, 27 mmol). The solution is stirred at r.t. for 20 h, concentrated under vacuum, and then dissolved in 100 mL of EtOAc—2.5% aq. $NaHCO_3$ (1:1). The layers are separated and the aqueous phase is extracted with EtOAc (2×50 mL). The combined organic layers are washed with brine, and dried ($MgSO_4$). Solvent is removed under vacuum to afford the crude title compound as an oil that is used directly without further purification.

Step 6. Preparation of [[(5S)-3-[4-[2,3-dihydro-1,1-dioxido-6-(trifluoroacetyl)-4H-1,4-thiazin-4-yl]phenyl]-2-oxo-5-oxazolidinyl]methyl]carbamic acid, 1,1-dimethylethyl ester.

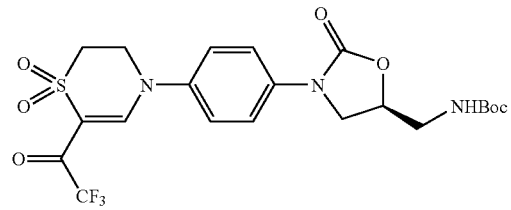

m-Chloroperoxybenzoic acid (4.8 g of a 60% Aldrich material, 17.0 mmol) is added to a cooled (0° C.) solution of the product from Step 5 (6.7 mmol) in DCM (140 mL), and the mixture is stirred at r.t. for 2 h. The reaction mixture is then quenched by the addition of 3 mL of satd. $Na_2S_2O_3$. The mixture is poured into dilute $NaHCO_3$ and extracted three times with dichloromethane. The combined organic extracts are washed with satd. $NaHCO_3$, brine and dried ($MgSO_4$), filtered and concentrated to provide the title compound, which is used in the next step without further purification.

Step 7. Preparation of [[(5S)-3-[4-(2,3-dihydro-1,1-dioxido-4H-1,4-thiazin-4-yl)phenyl]-2-oxo-5-oxazolidinyl]methyl]carbamic acid, 1,1-dimethylethyl ester.

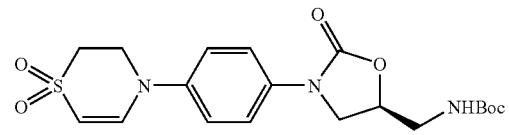

The crude sulfone prepared in Step 6 (6.7 mmol) is suspended in 220 mL of MeOH-acetonitrile (2:1) and heated to reflux. Solid $K_2CO_3$ (3.4 g, 25 mmol) is then added, and the mixture stirred at reflux for 2 h. Upon cooling, the solution is filtered and the filtrate concentrated. The residue is dissolved in 50 mL of EtOAc—2.5% aq. $NaHCO_3$ (1:1), the layers separated, and the aqueous phase extracted with more ethyl acetate. The combined organic layers are washed with brine and dried ($MgSO_4$), filtered and concentrated. The resulting crude product is purified by column chromatography (0–2% MeOH—$CH_2Cl_2$) provided the title compound as a foam.

Step 8. Preparation of N-[[(5S)-3-[4-(2,3-dihydro-1,1-dioxido-4H-1,4-thiazin-4-yl)phenyl]-2-oxo-5-oxazolidinyl]methyl]-2,2-difluoroethanethioamide.

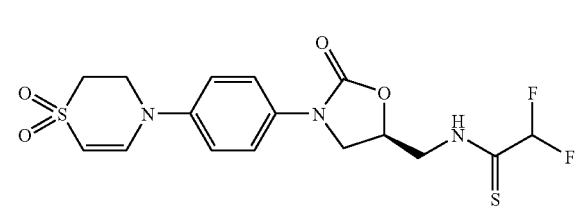

Trimethylsilyl trifluoromethanesulfonate (0.26 mL, 1.41 mmol) is added slowly over 15 min to a solution of the product from Step 7 (0.30 g, 0.71 mmol) and 2,6-lutidine (0.25 mL, 2.1 mmol) in dichloromethane (1.5 mL). The solution is stirred at room temperature for 1 h and then treated with methanol (1 mL). After 30 min, the solution is concentrated and redissolved in methanol (4 mL) and diisopropylethyl amine (0.38 mL, 2.1 mmol) is added. A solution of difluoro-thioacetic acid O-(3,3-diphenyl-propyl) ester (0.325 g, 0.71 mmol) in dichloromethane (0.5 mL) is then added and the solution stirred for 20 h at room temperature. The reaction mixture is then concentrated and the residue purified by column chromatography (0–1% MeOH-DCM) to provide the title compound.

MS (m/z): [M+H]$^+$=418. $^1$H NMR (300 MHz, DMSO-d$_6$): 3.3–3.4 (m, 2H), 3.86 (tr, J=9 Hz, 1H), 3.97 (m, 2H), 4.17–4.21 (m, 3H), 5.02 (m, 1H), 5.40 (d, J=9 Hz, 1H), 6.50 (t, J=56 Hz, 1H), 7.25 (d, J=9 Hz, 1H), 7.29 (d, J=9 Hz, 2H), 7.54 (d, J=9 Hz, 2H), 11.14 (s, 1H).

Example 25

Preparation of 2,2-dichloro-N-[[(5S)-3-[4-(2,3-dihydro-1,1-dioxido-4H-1,4-thiazin-4-yl)phenyl]-2-oxo-5-oxazolidinyl]methyl]acetamide

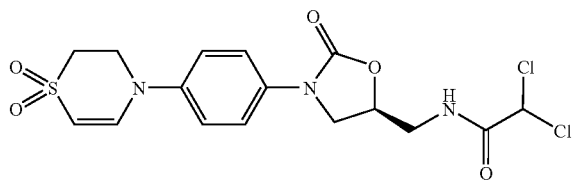

Following the procedures in Step 8 of Example 24 but using dichloroacetic anhydride (0.71 mmol) in pyridine (0.75 mL) as an acylating agent and purification by column chromatography (0–2% MeOH-DCM) gives the title compound.

MS (m/z): [M+H]$^+$=434. $^1$H NMR (300 MHz, CD$_3$OD): 3.30–3.35 (m, 2H), 3.69–3.71 (m, 2H), 3.83–3.88 (m, 1H), 4.13 (t, J=9 Hz, 1H), 4.28–4.32 (m, 2H), 4.84–4.88 (m, 1H), 5.40 (d, J=9 Hz, 1H), 6.05 (s, 1H), 6.98 (d, J=9 Hz, 1H), 7.14 (d, J=9 Hz, 2H), 7.54 (d, J=9 Hz, 2H)

Example 26

Preparation of N-[[(5S)-3-[4-(2,3-dihydro-1,1-dioxido-4H-1,4-thiazin-4-yl)phenyl]-2-oxo-5-oxazolidinyl]methyl]-2,2-difluoroacetamide

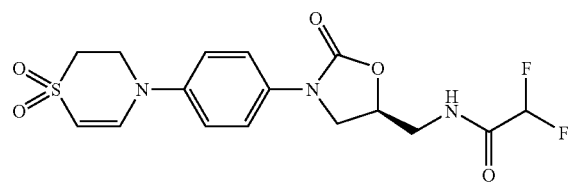

Following the procedures in Step 8 of Example 24 but using ethyl difluoroacetate (1.03 mmol) in methanol (3 mL) and triethylamine (1.03 mmol) as an acylating reagent and purification by column chromatography (0–3% MeOH-DCM) gives the title compound.

MS (m/z): [M+H]$^+$=402. $^1$H NMR (300 MHz, DMSO-d$_6$): 3.3–3.4 (m, 2H), 3.51–3.55 (m, 2H), 3.75–3.80 (m, 1H), 4.12–4.21 (m, 3H), 4.77–4.82 (m, 1H), 5.40 (d, J=9 Hz, 1H), 6.25 (tr, J=53 Hz, 1H), 7.25 (d, J=9 Hz, 1H), 7.29 (d, J=9 Hz, 2H), 7.52 (d, J=9 Hz, 2H), 9.18 (t, J=6 Hz, 1H).

Example 27

Preparation of N-[[(5S)-3-[4-(2,3-dihydro-1,1-dioxido-4H-1,4-thiazin-4-yl)-3,5-difluorophenyl]-2-oxo-5-oxazolidinyl]methyl]-2,2-difluoroethanethioamide

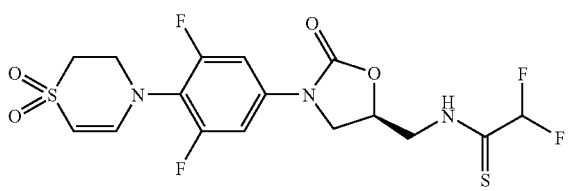

Step 1. Preparation of (S)-[[3-[4-(2,3-dihydro-1,1-dioxido-4H-1,4-thiazin-4-yl)-3,5-difluorophenyl]-2-oxo-5-oxazolidinyl]methyl]carbamic acid, 1,1-dimethylethyl ester.

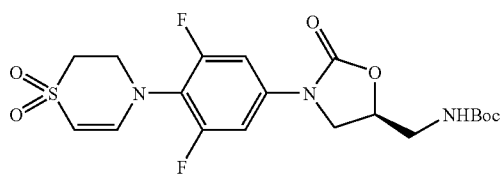

A solution of the product of Step 1 of Example 8 (1.05 g, 2.9 mmol) in DMF (2 mL) is cooled at 0° C. and treated with (3-chloro-2-hydroxy-propyl)-carbamic acid tert-butyl ester (0.76 g, 7.3 mmol) and then lithium tert-butoxide (7.25 mL of a 1.0 M solution in THF) dropwise over 15 min. The reaction mixture is stirred for 20 h at room temperature and then treated with 10 mL of satd. NH$_4$Cl and 15 mL of H$_2$O. The solution is extracted with three portions of dichloromethane and the combined organic phases washed with H$_2$O, brine and dried (MgSO$_4$), filtered and concentrated. The crude product is purified by column chromatography (0–1% MeOH-DCM) to provide the title compound as a white foam. Yield 0.92 g (69%).

Step 2. Preparation of N-[[(5S)-3-[4-(2,3-dihydro-1,1-dioxido-4H-1,4-thiazin-4-yl)-3,5-difluorophenyl]-2-oxo-5-oxazolidinyl]methyl]-2,2-difluoroethanethioamide.

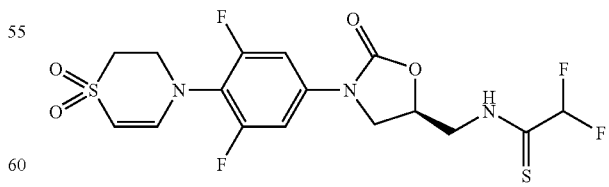

Trimethylsilyl trifluoromethanesulfonate (0.39 mL, 2.15 mmol) is added slowly over 15 min to a solution of (S)-{3-[4-(1,1-dioxo-2,3-dihydro-1H-1☐$^6$-[1,4]thiazin-4-yl)-3,5-difluoro-phenyl]-2-oxo-oxazolidin-5-ylmethyl}-carbamic acid tert-butyl ester (0.50 g, 1.08 mmol) and 2,6-lutidine (0.38 mL, 3.2 mmol) in dichloromethane (2.5 mL). The solution is stirred at room temperature for 1 h and then treated with methanol (1 mL). After 30 min, the solution is concentrated. A portion of the crude amine (0.65 mmol) is dissolved in methanol (6 mL) and diisopropylethylamine (0.35 mL, 1.95 mmol) is added. A solution of difluorothioacetic acid O-(3,3-diphenyl-propyl) ester (0.30 g, 0.97 mmol) in dichloromethane (1 mL) is then added and the solution stirred for 20 h at room temperature. The reaction mixture is then concentrated and the residue purified by column chromatography (0–1% MeOH-DCM) to provide the title compound.

MS (m/z): [M+H]$^+$=454. $^1$H NMR (300 MHz, DMSO-d$_6$): 3.3 (m, 2H), 3.83–3.88 (m, 1H), 3.98–4.03 (m, 4H), 4.20 (tr, J=9 Hz, 1H), 5.04–5.08 (m, 1H), 5.48 (d, J=9 Hz, 1H), 6.50 (tr, J=56 Hz, 1H), 6.93 (d, J=9 Hz, 1H), 7.45 (d, J=11 Hz, 2H), 11.1 (s, 1H).

Example 28

Preparation of 2,2-dichloro-N-[[(5S)-3-[4-(2,3-dihydro-1,1-dioxido-4H-1,4-thiazin-4-yl)-3,5-difluorophenyl]-2-oxo-5-oxazolidinyl]methyl]acetamide

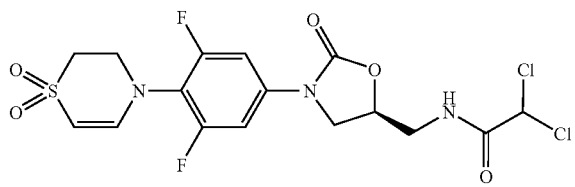

The title compound is obtained by following the procedures in Example 27 but using dichloroacetic anhydride (0.87 mmol) in pyridine (1 mL) as an acylating reagent and carrying out purification by column chromatography (0–2% MeOH-DCM).

MS (m/z): [M+H]$^+$=470. $^1$H NMR (300 MHz, DMSO-d$_6$): 3.34 (m, 2H), 3.54 (t, J=6 Hz, 2H), 3.71–3.77 (m, 1H), 3.98–4.02 (m, 2H), 4.16 (t, J=9 Hz, 1H), 4.83–4.88 (m, 1H), 5.47 (d, J=9 Hz, 1H), 6.48 (s, 1H), 6.93 (d, J=9 Hz, 1H), 7.44 (d, J=11 Hz, 2H), 8.98 (t, J=6 Hz, 1H).

Example 29

Preparation of N-[[(5S)-3-[4-(2,3-dihydro-1,1-dioxido-4H-1,4-thiazin-4-yl)-3,5-difluorophenyl]-2-oxo-5-oxazolidinyl]methyl]-2,2-difluoroacetamide

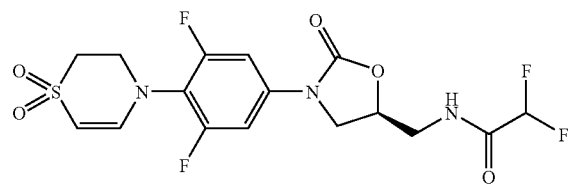

The title compound is obtained by following the procedures in Example 27 but using ethyl difluoroacetate (1.08 mmol) in methanol (4 mL) and diisopropyl-ethylamine (2.15 mmol) as an acylating reagent and carrying out purification by column chromatography (0–1% MeOH-DCM).

MS (m/z): [M+H]$^+$=438. $^1$H NMR (300 MHz, CD$_3$OD): 3.35–3.37 (m, 2H), 3.63–3.70 (m, 2H), 3.79–3.85 (m, 1H), 4.14 (t, J=9 Hz, 1H), 4.15–4.17 (m, 2H), 4.84–4.90 (m, 1H), 5.44 (d, J=9 Hz, 1H), 5.98 (t, J=54 Hz, 1H), 6.68 (d, J=9 Hz, 1H), 7.35 (d, J=10, 2H).

Example 30

Preparation of N-({(5S)-3-[4-(1,1-dioxido-3,4-dihydro-2H-thiopyran-4-yl)-3,5-difluorophenyl]-2-oxo-1,3-oxazolidin-5-yl}methyl)-2,2-difluoroacetamide

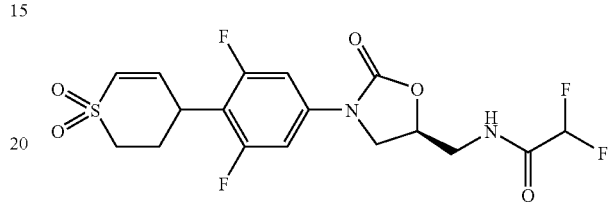

Step 1. Preparation of (5S)-5-(aminomethyl)-3-[4-(1,1-dioxido-3,4-dihydro-2H-thiopyran-4-yl)-3,5-difluorophenyl]-1,3-oxazolidin-2-one monohydrochloride.

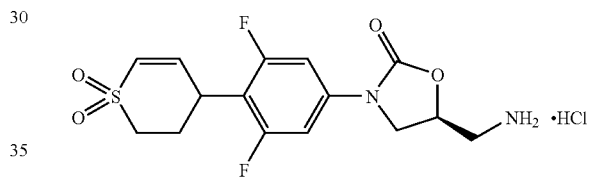

N-[[(5S)-3-[4-(3,4-dihydro-1,1-dioxido-2H-thiopyran-4-yl)-3,5-difluorophenyl]-2-oxo-5-oxazolidinyl]methyl]acetamide, prepared as described in Example 20 (1.60 g, 3.99 mmol) was suspended in a mixture of concentrated hydrochloric acid (15 ml) and methanol (45 ml), and heated at 70° C. overnight. The reaction mixture was evaporated to dryness to give white solid which is used directly in the next step (1.6 g, 99%).

Step 2. Preparation of N-({(5S)-3-[4-(1,1-dioxido-3,4-dihydro-2H-thiopyran-4-yl)-3,5-difluorophenyl]-2-oxo-1,3-oxazolidin-5-yl}methyl)-2,2-difluoroacetamide.

(5S)-5-(aminomethyl)-3-[4-(1,1-dioxido-3,4-dihydro-2H-thiopyran-4-yl)-3,5-difluorophenyl]-1,3-oxazolidin-2-one monohydrochloride from Step 1 (0.400 g, 1.02 mmol), ethyl difluoroacetate (0.633 g, 5.1 mmol), and triethylamine (0.284 ml, 2.04 mmol) in methanol (8 ml) were stirred at room temperature overnight. The reaction mixture was evaporated to dryness and the residue purified by PTLC (10% methanol/dichloromethane) to give white solid (0.36 g, 80%).

MS (m/z): [M+H]$^+$=437. $^1$H NMR (300 Mhz, DMSO): 2.27–2.48 (m, 2H), 3.31–3.40 (m, 1H), overlapping 3.52 (t, J=5.2 hz, 1H) and 3.52–3.59 (m, 1H), 3.76 (dd, J=7.1, 9.1 hz, 1H), 4.07–4.16 (m, 2H), 4.78–4.86 (m, 1H), 6.24 (t, J=53.6 hz, 1H), 6.44–6.49 (m, 1H), 6.70 (d tr, J=2.7, 11 hz, 1H), 7.30 (s, 1H), 7.34 (s, 1H), 9.16 (t, J=5.7 hz, 1H).

Example 31

Preparation of 2,2-dichloro-N-({(5S)-3-[4-(1,1-di-oxido-3,4-dihydro-2H-thiopyran-4-yl)-3,5-difluorophenyl]-2-oxo-1,3-oxazolidin-5-yl}methyl)acetamide

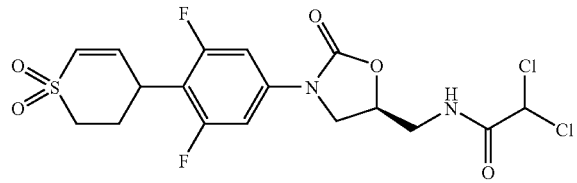

The crude amine hydrochloride prepared in Step 1 of Example 20A (0.400 g, 1.02 mmol), ethyl dichloroacetate (0.63 ml, 5.1 mmol), and triethylamine (0.28 ml, 2.04 mmol) in methanol (8 ml) were stirred at room temperature overnight. The reaction mixture was evaporated to dryness and the residue purified by PTLC (10% methanol/dichloromethane) to give white solid (0.34 g, 72%).

MS (m/z): $[M+H]^+$=469. $^1$H NMR (300 Mhz, DMSO): 2.26–2.48 (m, 2H), 3.33–3.41 (m, 1H), overlapping 3.52 (t, J=4.9 hz, 1H) and 3.55 (m, 1H), 3.73 (dd, J=6.6, 9.3 hz, 1H), 4.09–4.17 (m, 2H), 4.79–4.87 (m, 1H), overlapping 6.46 (m, 1H) and 6.47 (s, 1H), 6.70 (d tr, J=2.5, 11 hz, 1H), 7.30 (s, 1H), 7.33 (s, 1H), 8.97 (t, J=5.8 hz, 1H).

Example 32

Preparation of N-({(5S)-3-[4-(1,1-dioxido-3,4-dihydro-2H-thiopyran-4-yl)-3,5-difluorophenyl]-2-oxo-1, 3-oxazolidin-5-yl}methyl)-2,2-difluoroethanethioamide

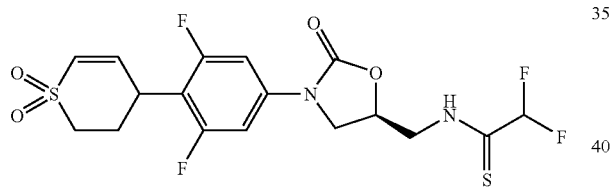

The crude amine hydrochloride prepared in Step 1 of Example 20A (0.400 g, 1.02 mmol), difluorothioacetic acid, O-(3,3-diphenyl-propyl) ester (0.375 g, 1.22 mmol), and triethylamine (0.28 ml, 2.04 mmol) in methanol (8 ml) were stirred at room temperature overnight. The reaction mixture was evaporated to dryness and the residue purified by PTLC (10% methanol/dichloromethane) to give white solid (0.35 g, 75%).

MS (m/z): $[M+H]^+$=453. $^1$H NMR (300 Mhz, DMSO): 2.26–2.46 (m, 2H), 3.33–3.38 (m, 1H), 3.49–3.58 (m, 1H), 3.83 (dd, J=6.6, 9.3 hz, 1H), 3.95–3.97 (m, 2H), 4.08–4.20 (m, 2H), 5.00–5.08 (m, 1H), overlapping 6.45–6.49 (m, 1H) and 6.49 (t, J=55 hz, 1H), 6.67–6.72 (m, 1H), 7.31 (s, 1H), 7.35 (s, 1H), 11.1 (s, 1H).

What is claimed is:

1. A compound of formula I

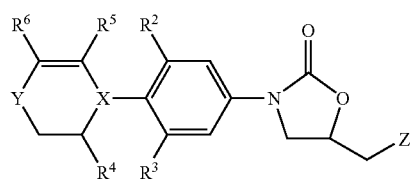

I or a pharmaceutically acceptable salt thereof wherein:

Y is
(a) —S(=O)$_n$—,
(b) —S(=NR$^8$)—, or
(c) —S(=NR$^8$)(=O)—;

Z is
(a) —NHC(=O)R$^1$,
(b) —NHC(=S)R$^1$,
(c) —NH-het$^1$,
(d) —O-het$^1$,
(e) —S-het$^1$, or
(f) -het$^2$ R$^1$ is
(a) —H,
(b) —NH$^2$,
(c) —NHC$_{1-4}$alkyl,
(d) —C$_{1-4}$alkyl,
(e) —C$_{2-4}$alkenyl,
(f) —(CH$_2$)$_n$C(=O)C$_{1-4}$alkyl,
(g) —OC$_{1-4}$alkyl,
(h) —SC$_{1-4}$alkyl, or
(i) —(CH$_2$)$_n$C$_{3-6}$cycloalkyl;

R$^2$ and R$^3$ are independently
(a) —H,
(b) —Cl,
(c) —F,
(d) —CH$_3$,
(e) —NH$_2$, or
(f) —OH;

R$^4$ is
(a) H,
(b) C$_{1-4}$alkyl,
(c) OC$_{1-4}$alkyl,
(d) SC$_{1-4}$alkyl, or
(e) NHC$_{1-4}$alkyl;

R$^5$ is
(a) H,
(b) C$_{1-4}$alkyl,
(c) OC$_{1-4}$alkyl,
(d) SC$_{1-4}$alkyl, or
(e) NHC$_{1-4}$alkyl;

R$^6$ is
(a) —H,
(b) —F,
(c) —Cl,
(d) —NH$_2$,
(e) —OH,
(f) —CN,
(g) —C$_{1-4}$alkyl,
(h) —OC$_{1-4}$alkyl,
(i) —C$_{1-4}$alkyl-W—C$_{1-4}$alkyl,
(j) —NHC$_{1-4}$alkyl,
(k) —(CH$_2$)$_n$C$_{3-6}$cycloalkyl,
(l) —C(=O)C$_{1-4}$alkyl,
(m) —OC(=O)C$_{1-4}$alkyl,
(n) —C(=O)OC$_{1-4}$alkyl,
(o) —S(O)$_n$C$_{1-4}$alkyl, or
(p) —C(=O)NHC$_{1-4}$alkyl;

R$^8$ is
(a) —H,
(b) —C$_{1-4}$alkyl,
(c) —C(=O)C$_{1-4}$alkyl,
(d) —C(=O)NHC$_{1-4}$alkyl,
(e) —OC(=O)C$_{1-4}$alkyl,
(f) —C(=O)OC$_{1-4}$alkyl, or
(g) —S(O)$_n$C$_{1-4}$alkyl, or
(h) —C$_{1-4}$alkyl-W—C$_{1-4}$alkyl;

W is O or S;

aryl is phenyl, biphenyl, or naphthyl, optionally substituted with halo, —$C_{1-4}$alkyl, —OH, —$OC_{1-4}$alkyl, —$S(O)_n$ $C_{1-4}$alkyl, and —$C_{1-4}$alkyl-$NH_2$;

$het^1$ is a C-linked five-(5) or six-(6) membered heterocyclic ring having 1–4 heteroatoms selected from the group consisting of oxygen, sulfur, and nitrogen;

$het^2$ is a N-linked five-(5) or six-6) membered heterocyclic ring having at least one nitrogen atom, and optionally having one oxygen or sulfur atom;

at each occurrence n is independently 0, 1, or 2; and at each occurrence, alkyl, alkenyl, or cycloalkyl is optionally substituted with one, two, or three halo, OH, $OC_{1-4}$alkyl, aryl, $het^1$, or $het^2$.

2. A compound of claim 1 which is a compound of formula II

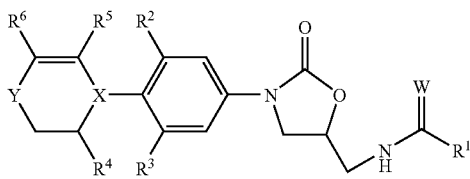

wherein W is O or S.

3. A compound of claim 2 which is a compound of formula III

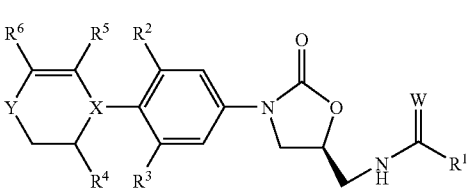

wherein $R^4$, $R^5$ and $R^6$ are —H.

4. A compound of claim 3 wherein $R^2$ and $R^3$ are independently —H or —F.

5. A compound of claim 3 wherein $R^1$ is —$C_{1-4}$alkyl, optionally substituted with one, two or three —F, or —Cl.

6. A compound of claim 4 wherein $R^1$ is —$CHF_2$, —$CHCl_2$, or —$CH_2CF_3$.

7. A compound of claim 4 wherein $R^1$ is —$CH_3$, —$CH_2CH_3$, or cyclopropyl.

8. A compound of claim 4 wherein $R^1$ is —CH=CH-aryl, or —$CH_2C$(=O)$C_{1-4}$alkyl.

9. A compound of claim 3 wherein Y is —S—, —S(=O)—, or —S(=O)$_2$—.

10. A compound of claim 3 wherein Y is —S(=$NR^8$)—, or —S(=$NR^8$)(=O)—.

11. A compound of claim 1 which is (1) N-[[(5S)-3-[4-(2,3-dihydro-1,1-dioxido-4H-1,4-thiazin-4-yl)-3-fluorophenyl]-2-oxo-5-oxazolidinyl]methyl]acetamide, (2) N-[[(5S)-3-[4-(2,3-dihydro-1,1-dioxido-4H-1,4-thiazin-4-yl)-3,5-difluorophenyl]-2-oxo-5-oxazolidinyl]methyl]acetamide, (3) N-[[(5S)-3-[4-(2,3-dihydro-1,1-dioxido-4H-1,4-thiazin-4-yl)-3fluorophenyl]-2-oxo-5-oxazolidinyl]methyl]-2,2-difluoroethanethionamide, (4) 2,2-dichloro-N-[[(5S)-3-[4-(2,3-dihydro-1,1-dioxido-4H-1,4-thiazin-4-yl)-3-fluorophenyl]-2-oxo-5-oxazolidinyl]methyl]acetamide, (5) N-[[(5S)-3-[4-(2,3-dihydro-1,1-dioxido-4H-1,4-thiazin-4-yl)-3-fluorophenyl]-2-oxo-5-oxazolidinyl]methyl]-2,2-difluoroacetamide, (6) N-[[(5S)-3-[4-(2,3-dihydro-1,1-dioxido-4H-1,4-thiazin-4-yl)phenyl]-2-oxo-5-oxazolidinyl]methyl]-2,2-difluoroethanethioamide, (7) 2,2-dichloro-N-[[(5S)-3-[4-(2,3-dihydro-1,1-dioxido-4H-1,4-thiazin-4-yl)phenyl]-2-oxo-5-oxazolidinyl]methyl]acetamide, (8) N-[[(5S)-3-[4-(2,3-dihydro-1,1-dioxido-4H-1,4-thiazin-4-yl)phenyl]-2-oxo-5-oxazolidinyl]methyl]-2,2-difluoroacetamide, (9) N-[[(5S)-3-[4-(2,3-Dihydro-1,1-dioxido-4H-1,4-thiazin-4-yl)-3,5-difluorophenyl]-2oxo-5-oxazolidinyl]methyl]-2,2-difluoroethanethioamide,

(10) 2,2-dichloro-N-[[(5S)-3-[4-(2,3-dihydro-1,1-dioxido-4H-1,4-thiazin-4-yl)-3,5-difluorophenyl]-2-oxo-5-oxazolidinyl]methyl]acetamide, or

(11) N-[[(5S)-3-[4-(2,3-dihydro-1,1-dioxido-4H-1,4-thiazin-4-yl)-3,5-difluorophenyl]-2-oxo-5-oxazolidinyl]methyl]-2,2-difluoroacetamide.

12. A compound of claim 1 which is (1) N-[[(5S)-3-[4-(2,3-dihydro-1,1dioxido-4H-1,4-thiazin-4-yl)-3-fluorophenyl]-2oxo-5-oxazolidinyl]methyl]acetamide, (2) 2,2-dichloro-N-[[(5S)-3-[4-(2,3-dihydro-1,1-dioxido-4H-1,4-thiazin-4-yl)-3-fluorophenyl]-2-oxo-5-oxazolidinyl]methyl]acetamide, (3) 2,2-clichloro-N-[[(5S)-3-[4-(2,3-dihydro-1,1-dioxido-4H-1,4-thiazin-4-yl)phenyl]-2-oxo-5-oxazolidinyl]methyl]acetamide, (4) N-[[(5S)-3-[4-(2,3-dihydro-1,1-dioxido-4H-1,4-thiazin-4-yl)3,5-difluorophenyl]-2-oxo-5-oxazolidinyl]methyl]acetamide, (5) N-[[(5S)-3-[4-(2,3-dihydro-1,1-dioxido-4H-1,4-thiazin-4-yl)-3-fluorophenyl]-2oxo-5-oxazolidinyl]methyl]-2,2-difluoroethanethioamide, (6) N-[[(5S)-3-[4-(2,3 -dihydro-1,1-dioxido-4H-1,4-thiazin-4-yl)-3-fluoropheyl]-2-oxo-5-oxazolidinyl]methyl]-2,2-difluoroacetamide, (7) N-[[(5S)-3-[4-(2,3-dihydro-1,1-dioxido-4H-1,4-thiazin-4-yl)phenyl]-2-oxo-5-oxazolidinyl]methyl]-2,2-difluoroethanethioamide, or (8) 2,2-dichloro-N-[[(5S)-3-[4-(2,3-dihydro-1,1-dioxido-4H-1,4-thiazin-4-yl)-3,5-difluorophenyl]-2-oxo-5-oxazolidinyl]methyl]acetamide.

13. A compound of claim 1 which is (1) N-[[(5S)-3-[4-(2,3-dihydro-1,1-dioxido-4H-1,4-thiazin-4-yl)-3-fluorophenyl]-2-oxo-5-oxazolidinyl]methyl]acetamide, or (2) 2,2-dichloro-N-[[(5S)-3-[4-(2,3-dihydro-1,1-dioxido-4H-1,4-thiazin-4-yl)-3-fluorophenyl]-2-oxo-5-oxazolidinyl]methyl]acetamide.

14. A compound of claim 1 which is a compound of formula IV

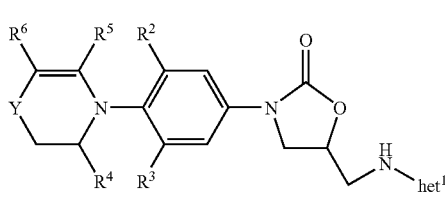

IV or a pharmaceutically acceptable salt thereof wherein Y is —S—, —S(=O)—, or —S(=O)$_2$—.

15. A compound of claim 14 wherein $R^2$ and $R^3$ are independently —H or —F; $R^4$, $R^5$, and $R^6$ are —H; and het$^1$ is isoxazolyl, 1,2,5-thiadiazolyl, or pyridyl.

16. A compound of claim 1 which is a compound of formula V

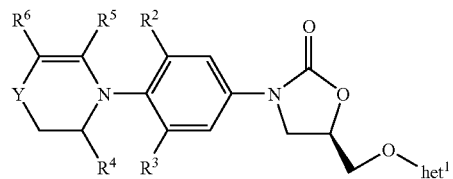

V or a pharmaceutically acceptable salt thereof wherein Y is —S—, —S(=O)—, or —S(=O)$_2$—.

17. A compound of claim 16 wherein $R_2$ and $R_3$ are independenfly —H or —F; $R^4$, $R^5$, and $R^6$ are —H; and het$^1$ is isoxazolyl, 1,2,5-thiadiazolyl, or pyridyl.

18. A compound of claim 1 which is a compound of formula VII

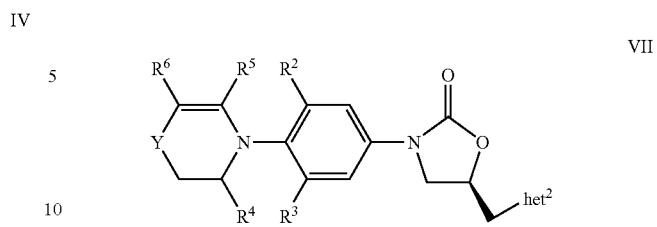

VII or a pharmaceutically acceptable salt thereof wherein wherein Y is —S—, —S(=O)—, or —S(=O)$_2$—.

19. A compound of claim 18 wherein $R^2$ and $R^3$ are independently —H or —F; $R^4$, $R^5$, and $R^6$ are —H; and het$^2$ is pyrrolyl, imidazolyl, pyrazolyl, triazolyl, tetrazolyl or isoxazolinonyl.

20. A method for treating bacterial infections comprising: administering to a mammal in need for such treatment thereof an effective amount of a compound of claim 1.

21. The method of claim 20 wherein said compound of formula I is administered orally, parenterally, transdermally, topically, rectally, or intranasally in a pharmaceutical composition.

22. The method of claim 20 wherein said compound is administered in an amount of from about 0.1 to about 100 mg/kg of body weight/day.

23. The method of claim 20 wherein said compound is administered in an amount of from about 1 to about 50 mg/kg of body weight/day.

24. A pharmaceutical composition comprising a compound of claim 1 and a pharmaceutically acceptable carrier.

* * * * *